US011986325B2

United States Patent
Choi et al.

(10) Patent No.: US 11,986,325 B2
(45) Date of Patent: May 21, 2024

(54) TREATMENT INFORMATION DISPLAY DEVICE AND METHOD FOR DISPLAYING TREATMENT HISTORY ON IMAGE OF TEETH IN ACCUMULATED MANNER

(71) Applicant: Osstemimplant Co., Ltd., Seoul (KR)

(72) Inventors: Kyoo Ok Choi, Seoul (KR); Soo Gil Kim, Seoul (KR)

(73) Assignee: Osstemimplant Co., Ltd., Seoul (KR)

( * ) Notice: Subject to any disclaimer, the term of this patent is extended or adjusted under 35 U.S.C. 154(b) by 106 days.

(21) Appl. No.: 17/618,726

(22) PCT Filed: Jun. 10, 2020

(86) PCT No.: PCT/KR2020/007511
§ 371 (c)(1),
(2) Date: Dec. 13, 2021

(87) PCT Pub. No.: WO2020/251255
PCT Pub. Date: Dec. 17, 2020

(65) Prior Publication Data
US 2022/0240868 A1    Aug. 4, 2022

(30) Foreign Application Priority Data

Jun. 13, 2019  (KR) ......................... 10-2019-0069915
Jun. 9, 2020  (KR) ......................... 10-2020-0069786

(51) Int. Cl.
*G06F 17/00*  (2019.01)
*A61B 5/00*  (2006.01)
(Continued)

(52) U.S. Cl.
CPC ............ *A61B 5/743* (2013.01); *G06F 3/0482* (2013.01); *G06F 3/04855* (2013.01); *G16H 30/40* (2018.01)

(58) Field of Classification Search
CPC ............ A61B 5/743; A61B 6/463; A61B 6/14; G16H 30/40; G16H 10/60; G16H 50/20; G16H 15/00
(Continued)

(56) References Cited

U.S. PATENT DOCUMENTS 6,068,482 A * 5/2000 Snow .................. A61C 9/00
433/223
6,227,850 B1 * 5/2001 Chishti ............... A61C 9/0053
433/213
(Continued)

FOREIGN PATENT DOCUMENTS

JP     2004-005565 A      1/2004
KR     100453509 B1     10/2004
(Continued)

OTHER PUBLICATIONS

Rykov, Three Dimensional Interactive Dental Charting, OULU University of Applied Sciences, 2012 (Year: 2012).*
(Continued)

*Primary Examiner* — Stephen S Hong
*Assistant Examiner* — Matthew J Ludwig
(74) *Attorney, Agent, or Firm* — Downs Rachlin Martin PLLC

(57) ABSTRACT

Disclosed are treatment information display device and method for displaying treatment history on an image of teeth in an accumulated manner. The treatment information display method enables a user to recognize at once a past treatment history, a current treatment status, and a future treatment plan by displaying, on the image of teeth, treatment information for the past, present, and future. In addition, the treatment information display method can provide the user with pieces of treatment information displayed on different images of teeth, by displaying, in an accumulated
(Continued)

manner, the pieces of treatment information displayed on a plurality of teeth images.

16 Claims, 15 Drawing Sheets

(51) Int. Cl.
   *G06F 3/0482* (2013.01)
   *G06F 3/04855* (2022.01)
   *G16H 30/40* (2018.01)
(58) Field of Classification Search
   USPC .......................................................... 715/833
   See application file for complete search history.

(56) References Cited

U.S. PATENT DOCUMENTS

| | | | | |
|---|---|---|---|---|
| 7,010,153 | B2* | 3/2006 | Zimmermann | G16H 30/20 382/305 |
| 7,343,305 | B2* | 3/2008 | Benn | G16H 30/40 433/215 |
| 7,452,210 | B2* | 11/2008 | Charles | A61C 19/00 434/430 |
| 8,113,829 | B2* | 2/2012 | Sachdeva | A61C 9/0046 433/24 |
| 8,177,551 | B2* | 5/2012 | Sachdeva | A61C 9/0046 433/2 |
| 9,510,918 | B2* | 12/2016 | Sanchez | A61C 7/14 |
| 10,390,913 | B2* | 8/2019 | Sabina | A61B 6/145 |
| 11,147,652 | B2* | 10/2021 | Mason | G16Z 99/00 |
| 11,389,131 | B2* | 7/2022 | Tuzoff | A61B 6/51 |
| 11,701,208 | B2* | 7/2023 | Esbech | A61C 13/082 382/154 |
| 2005/0027172 | A1* | 2/2005 | Benavides | G16H 10/20 128/920 |
| 2006/0069591 | A1* | 3/2006 | Razzano | G16H 30/20 705/2 |
| 2009/0214089 | A1* | 8/2009 | Stookey | A61B 5/7445 382/128 |
| 2010/0036682 | A1* | 2/2010 | Trosien | G16H 20/30 705/3 |
| 2010/0121658 | A1* | 5/2010 | Kaminski | A61C 19/00 715/790 |
| 2013/0122468 | A1* | 5/2013 | Abrams | A61B 6/14 433/215 |
| 2014/0379356 | A1 | 12/2014 | Sachdeva et al. | |
| 2016/0124920 | A1* | 5/2016 | Golay | G06F 40/143 705/3 |
| 2018/0357766 | A1* | 12/2018 | Van Der Poel | A61B 5/0062 |
| 2019/0043607 | A1* | 2/2019 | Sears | G16H 30/20 |
| 2019/0159868 | A1* | 5/2019 | Chen | A61C 13/0004 |
| 2019/0175303 | A1* | 6/2019 | Akopov | A61C 7/002 |
| 2019/0269482 | A1* | 9/2019 | Shanjani | A61B 90/37 |
| 2019/0333622 | A1* | 10/2019 | Levin | G16H 20/30 |
| 2020/0015943 | A1* | 1/2020 | Reynard | G06T 19/00 |
| 2020/0306011 | A1* | 10/2020 | Chekhonin | G16H 50/50 |
| 2022/0084267 | A1* | 3/2022 | Ezhov | A61B 6/4085 |

FOREIGN PATENT DOCUMENTS

| | | |
|---|---|---|
| KR | 10-2011-0036387 A | 4/2011 |
| KR | 10-1298548 B1 | 8/2013 |
| KR | 10-2014-0120637 A | 10/2014 |
| KR | 10-2016-0142142 A | 12/2016 |
| KR | 101723654 B1 | 4/2017 |

OTHER PUBLICATIONS

Supplementary European Search Report corresponding to European Patent Application No. 20822034.3 dated Jun. 2, 2022 (9 pages).

* cited by examiner

FIG. 3

TREATMENT INFORMATION DISPLAY DEVICE AND METHOD FOR DISPLAYING TREATMENT HISTORY ON IMAGE OF TEETH IN ACCUMULATED MANNER

CROSS-REFERENCES TO RELATED APPLICATIONS

This application is a U.S. national phase application, pursuant to 35 U.S.C. § 371, of PCT/KR2020/007511, filed Jun. 10, 2020, designating the United States, which claims priority to Korean Application No. 10-2020-0069786, filed Jun. 9, 2020, and Korean Application No. 10-2019-0069915, filed Jun. 13, 2019. The entire contents of the aforementioned patent applications are incorporated herein by this reference.

TECHNICAL FIELD

The following description relates to a treatment information display method, and more particularly, to a device and a method for displaying treatment history including pieces of treatment information on a tooth area selected by a user in an image of teeth.

BACKGROUND ART

Recently, a number of medical institutions are using electronic medical records (EMR), and according to this trend, various treatment information is input into electronic charts during dental treatment.

The electronic chart, which is a treatment information display device according to a related art, may consist of a dental chart and a treatment information input window. A user selected a tooth and a tooth part from the dental chart, and input treatment information corresponding to the selected tooth in the treatment information input window.

However, since the treatment information display device according to the related art displays an image of teeth and the treatment information in different areas, the user has to continuously alternately look at a medical image of a patient and the electronic chart when inputting the treatment information, which is inconvenient because the gaze is dispersed. In addition, the treatment information display device according to the related art has an issue in that it is difficult to recognize a past treatment history, a current treatment status, or a future treatment plan.

DISCLOSURE OF THE INVENTION

Technical Goals

An aspect provides a device and method for allowing a user to recognize a past treatment history, a current treatment status, and a future treatment plan at once by displaying treatment information for the past, present, and future on an image of teeth.

Another aspect provides a device and a method for providing the user with pieces of treatment information displayed on different images of teeth, by displaying, in an accumulated manner, pieces of treatment information displayed on each of a plurality of teeth images.

Technical Solutions

According to an aspect, there is provided a treatment information display method including: displaying an image of a patient's teeth; displaying area dividing lines on the image of teeth, each of the area dividing lines for dividing an area of each of the teeth included in the image of teeth; receiving, through an interface, a user's selection of one of a plurality of areas divided according to the area dividing lines; and providing the user with treatment information of a tooth corresponding to the area identified according to the user's selection.

The providing of the user with the treatment information of the treatment information display method according to the aspect may include mapping pieces of treatment information corresponding to time information received from the user of pieces of treatment information of the tooth corresponding to the area to an area corresponding to the user's selection and displaying the same.

The providing of the user with the treatment information of the treatment information display method according to the aspect may include sorting the pieces of treatment information of the tooth corresponding to the area in chronological order, and selecting and displaying sequentially a preset number of pieces of information of the sorted pieces of treatment information.

The treatment information of the treatment information display method according to the aspect may include detailed information on treatment and summary information in which the size of information displayed on a display is reduced compared to the detailed information by summarizing the detailed information. The providing of the user with the treatment information may include providing the user with the summary information if the number of the pieces of treatment information of the tooth corresponding to the area is equal to or greater than a threshold value, and providing the user with the detailed information if the number of the pieces of treatment information of the tooth corresponding to the area is less than the threshold value.

The treatment information display method according to the aspect may further include, in the case of receiving the user's selection for the summary information through an interface, providing the user with the detailed information corresponding to the summary information.

The treatment information of the treatment information display method according to the aspect may include at least one of past treatment information including a diagnosis history or a treatment history generated for the tooth at a previous time based on the time at which the image of teeth is displayed, current treatment information including a diagnosis result for a current status of the tooth included in the image, and future treatment information including a treatment plan to be performed for the tooth at a later time based on the time at which the image of teeth is displayed.

The treatment information display method according to the aspect may further include receiving time information selected by the user through an interface; and searching for a tooth for which treatment information is generated within a time section included in the time information. The displaying of the area dividing lines on the image of teeth may include displaying the area of the searched tooth to be differentiated from that of an unsearched tooth.

The treatment information display method according to the aspect may further include receiving selected time input by the user through a navigation bar for allowing selection from the time at which the treatment information is initially generated to the time at which treatment of the patient is expected to be completed. The providing of the user with the treatment information may include selecting one of the past treatment information, the current treatment information, and the future treatment information from the treatment information of the tooth corresponding to the area according to movement of the navigation bar and a position at which the navigation bar stops moving and providing the same.

The treatment information display method according to the aspect may further include searching for a tooth for which the treatment information is generated before a time corresponding to a position where the navigation bar stops moving. The displaying of the area dividing lines on the image of teeth may include differentiating the color of the area or the area dividing line of the searched tooth, and a display effect to be applied to the area of the tooth from those of the area of an unsearched tooth and providing the user with the same.

The treatment information display method according to the aspect may further include receiving selected time input by the user through a navigation bar for allowing selection from the time at which the treatment information was initially generated to the time at which treatment of the patient is expected to be completed. The providing of the user with the treatment information may include choosing and providing one of the past treatment information, the current treatment information, and the future treatment information from the treatment information of the tooth corresponding to the area according to movement of the navigation bar and a position at which the navigation bar stops moving.

The treatment information display method according to the aspect may further include searching for a tooth for which the treatment information was generated before a time corresponding to a position where the navigation bar stops moving. The displaying of the area dividing lines on the image of teeth may include differentiating the color of the area or the area dividing line of the searched tooth, and a display effect to be applied to the area of the tooth from those of the area of an unsearched tooth and providing the user with the same.

The treatment information display method according to the aspect may further include displaying a list of diagnosis types or treatment types; receiving the user's selection of a diagnosis type or a treatment type through the interface; and searching for a tooth corresponding to the diagnosis type or treatment type selected by the user. The displaying of the area dividing lines on the image of teeth may include comprises differentiating the color of the area or the area dividing line of the searched tooth, and a display effect to be applied to the area of the tooth from those of the area of an unsearched tooth and providing the user with the same.

The treatment information display method according to the aspect may further include, in the case that the diagnosis type or treatment type selected by the user requires an image other than the image of teeth, mapping an image corresponding to the diagnosis type or treatment type selected by the user to the image of teeth and displaying the same.

The providing of the user with the treatment information of the treatment information display method according to the aspect may include displaying an image of a tooth corresponding to the area identified according to the user's selection; receiving a direction selected by a user on the image of the tooth through the interface; and selecting and further displaying one of past treatment information, current treatment information, and future treatment information of the tooth corresponding to the area, and images related to the tooth corresponding to the area according to the direction selected by the user.

The providing of the user with the treatment information of the treatment information display method according to the aspect may include displaying summary information obtained by statisticizing past treatment information, current treatment information, and future treatment information of a tooth corresponding to the area; in the case of receiving the user's selection of the summary information through the interface, providing one of a list of pieces of the past treatment information, a list of pieces of the current treatment information, and a list of pieces of the future treatment information to the user according to the user's selection; and in the case that one of the pieces of treatment information included in the list is selected by the user, providing the user with detailed information on the selected piece of treatment information.

According to another aspect, there is provided a treatment information display method including displaying the most recently generated image of teeth of images of teeth of a patient generated at different times; displaying area dividing lines on the image of teeth, each of the area dividing lines for dividing an area of each of teeth displayed on the image of teeth; receiving, through an interface, a user's selection of any one of a plurality of areas divided according to the area dividing lines; and collecting and providing the user with treatment information of a tooth corresponding to the area corresponding to the user's selection from each of the patient's images of teeth generated at different times.

The providing of the user with the treatment information of the treatment information display method according to the aspect may include mapping pieces of treatment information corresponding to time information received from the user of pieces of treatment information of the tooth corresponding to the area to an area corresponding to the user's selection and displaying the same.

The treatment information of the treatment information display method according to the aspect may include detailed information on treatment and summary information in which the size of information displayed on a display is reduced compared to the detailed information by summarizing the detailed information. The providing of pieces of treatment information to the user may include, if the number of pieces of treatment information of the tooth corresponding to the area is equal to or greater than a threshold value, providing the user with the summary information, and if the number of the pieces of treatment information of the tooth corresponding to the area is less than the threshold value, providing the user with the detailed information.

According to another aspect, there is provided a treatment information display device including a display configured to display an image of teeth of a patient and displaying area dividing lines on the image of teeth, each of the area dividing lines for dividing an area of each of teeth included in the image of teeth; and a processor configured to receive a user's selection of any one of a plurality of areas divided according to the area dividing lines through an interface, and provide the user with treatment information corresponding to the area identified according to the user's selection.

According to another aspect, there is provided a treatment information display device including a display configured to display the most recently generated image of teeth of images of teeth of a patient generated at different times, and display area dividing lines on the image of teeth, each of the area dividing lines for dividing an area of each of teeth displayed on the image of teeth; and a processor configured to receive a user's selection of any one of a plurality of areas divided according to the area dividing lines through an interface, and collect and provide the user with treatment information of a tooth corresponding to the area corresponding to the user's selection from each of the patient's images of teeth generated at different times.

Advantageous Effects

According to example embodiments, it is possible to provide the user with a treatment history for each tooth by displaying treatment information for the tooth in chronological order.

According to example embodiments, by differentiating a method of displaying the treatment information according to an attribute of the treatment information, it is possible to enable the user to easily recognize which attribute of a treatment result of the past, a current status of the tooth, and a treatment plan for the tooth the treatment information corresponds to.

According to example embodiments, it is possible to prevent an unnecessarily large amount of treatment information from obscuring the image of teeth by maintaining the number of pieces of treatment information displayed on the image of teeth below a predetermined number.

According to example embodiments, it is possible to increase the number of pieces of treatment information displayed in the same area by decreasing the size of each piece of treatment information displayed on the image of teeth.

BRIEF DESCRIPTION OF DRAWINGS

FIG. 3 is an example of a screen in which treatment information is displayed according to an example embodiment.

BEST MODE FOR CARRYING OUT THE INVENTION

Figure 1:
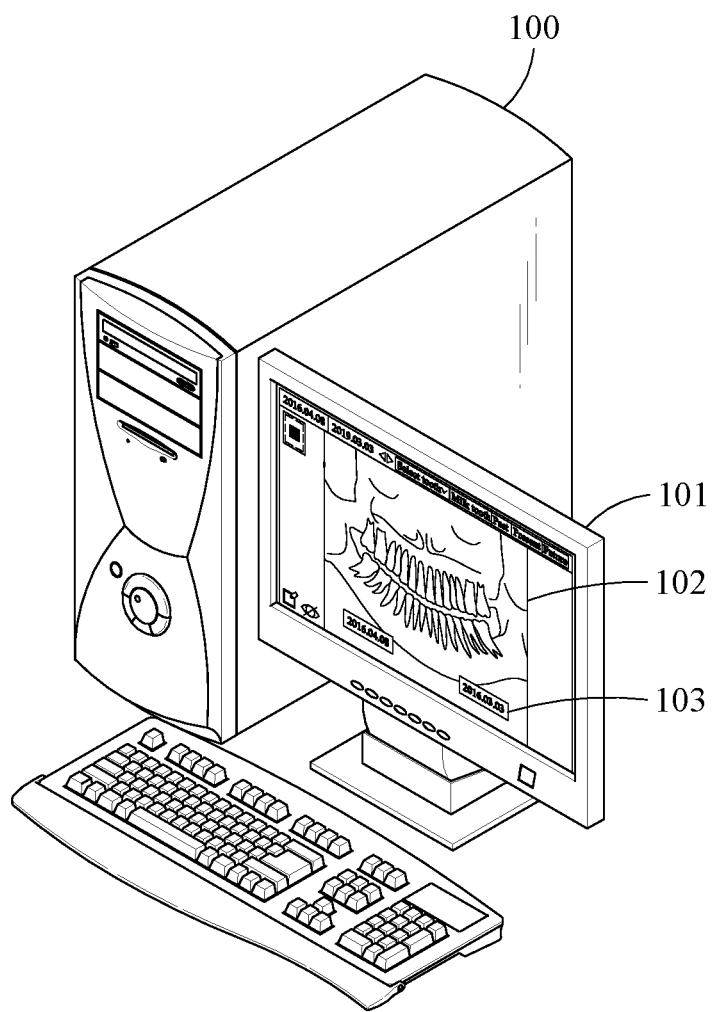
FIG. 1 is a diagram illustrating a treatment information display device according to an example embodiment.

Hereinafter, example embodiments will be described in detail with reference to the accompanying drawings. However, since various changes may be made to the example embodiments, the scope of the patent application is not limited by these example embodiments. It should be understood that all modifications, equivalents and substitutes for the example embodiments are included in the scope of the invention.

Terms used in the example embodiments are used for the purpose of description only, and should not be construed as limiting the invention. A singular expression includes a plural expression unless the context clearly indicates otherwise. It is to be understood that terms such as "comprise", "include", or "have" in the present specification are intended to indicate that a feature, a number, a step, an operation, an element, a component, or a combination thereof described in the specification exists, but does not preclude the possibility of the presence or addition of one or more other features, numbers, steps, operations, elements, components, or combinations thereof.

In addition, in the description with reference to the accompanying drawings, the same elements are indicated by the same reference numerals, and overlapping descriptions thereof will be omitted. In the description of an example embodiment, in the case that it is determined that a detailed description of a related known technology may unnecessarily obscure the gist of the example embodiment, the detailed description thereof will be omitted.

Hereinafter, example embodiments of the invention will be described in detail with reference to the accompanying drawings.

FIG. 1 is a diagram illustrating a treatment information display device according to an example embodiment.

A treatment information display device 100 displays an image of teeth 102 on a display 101 as shown in FIG. 1, and may display treatment information 103 matched to a tooth included in the image of teeth 102. For example, as shown in FIG. 1, the treatment information display device 100 may be a PC, a smart terminal, or a notebook computer. Also, the display 101 may be a monitor as shown in FIG. 1 or a display device included in the treatment information display device 100.

First, the treatment information display device 100 may display the image of teeth 102 of a patient on the display 101 as shown in FIG. 1. The display 101 may display area dividing lines, each of the area dividing lines for dividing an area of each of the teeth included in the image of teeth 102, on the image of teeth 102 according to a request of a processor of the treatment information display device 100.

The treatment information display device 100 may receive time information selected by a user through an interface. The time information may include at least one of the past corresponding to a previous time based on the time at which the image of teeth 102 is displayed, the present corresponding to the time at which the image of teeth 102 is displayed, and the future corresponding to a later time based on the time at which the image of teeth 102 is displayed. For example, the time information may be one of (past), (present), (future), (past, future), (past, present), (present, future), and (past, present, future). Further, the time information may be a predetermined time section selected by the user from the past or the future. For example, the time information may be information indicating a time section such as (2015-2019) or (2021-2023).

In this case, the treatment information display device 100 may search for a tooth for which treatment information is generated within a time section included in the time information. Then, the treatment information display device 100 displays the area of the searched tooth to be differentiated from that of an unsearched tooth so that the user can easily recognize the tooth for which the treatment information was generated within the time section.

For example, in the case that the time information is (2015-2019), the treatment information display device 100 may search for a tooth for which treatment information was generated between 2015 and 2019. Further, the treatment information display device 100 performs a process of highlighting, hatching, or shading only the area of the searched tooth, or displaying only the area of the searched tooth in a color different from that of the unsearched tooth, thereby allowing the user to identify the tooth for which the treatment information was generated between 2015 and 2019.

In addition, the treatment information display device 100 may receive the user's selection of one of a plurality of areas divided according to the area dividing lines through the interface. In this case, the treatment information display device 100 may provide the user with treatment information on a tooth corresponding to the area identified according to the user's selection.

For example, the treatment information display device 100 may map pieces of treatment information corresponding to the time information received from the user of pieces of treatment information of the tooth corresponding to the area to the area corresponding to the user's selection and display the same. Here, the treatment information may include at least one of past treatment information including a diagnosis history or a treatment history generated for the tooth at a previous time based on the time at which the image of teeth is displayed, current treatment information including a diagnosis result for a current status of the tooth included in the image of teeth 102, and future treatment information including a treatment plan to be performed on the tooth at a later time based on the time at which the image of teeth 102 is displayed.

In this case, the treatment information display device 100 may receive time information selected by the user through the interface. Further, the treatment information display device 100 may map treatment information corresponding to the time information of pieces of treatment information on the tooth corresponding to the area corresponding to the user's selection to the area and display the same. For example, in the case that the time information is one of (past), (present), and (future), the treatment information display device 100 may select one of the past treatment information, current treatment information, and future treatment information according to the time information, and map the selected treatment information to the area corresponding to the user's selection and display the same. Further, in the case that the time information indicates two or more different time sections such as (past, future), (past, present), (present, future), (past, present, future), the treatment information display device 100 may select a plurality of pieces of treatment information corresponding to the time information from the past treatment information, the current treatment information, and the future treatment information according to the time information. Then, the treatment information display device 100 may map the selected pieces of treatment information to the area corresponding to the user's selection and display the same.

In this case, the treatment information display device 100 may differentiate the color of the treatment information or a display effect to be applied to the treatment information according to the time information and provide the same to the user. For example, the treatment information display device 100 displays the past treatment information on a red background or in red text, the current treatment information on a blue background or in blue text, and the future treatment information on a green background or in green text.

Further, the treatment information display device 100 may sort the pieces of treatment information corresponding to the area in chronological order, and sequentially select and display a preset number of pieces of information of the sorted pieces of treatment information.

The treatment information may include detailed information and summary information about treatment. The summary information may be information in which the size of the information displayed on the display 101 is reduced compared to the detailed information by summarizing the detailed information.

For example, in the case that the detailed information includes an image showing a change in the appearance of a tooth, the summary information may include only a part of the image or an image whose size is downscaled. In addition, the detailed information may include all information about the patient's treatment, and the summary information may include only the date the patient was treated and the name of the treatment.

In other words, since the area required to display the treatment information displayed as the summary information on the display 101 is smaller than the area required to display the treatment information displayed as the summary information on the display 101, a larger number of pieces of treatment information may be displayed in the case of displaying the summary information on the display 100 than in the case of displaying the detailed information.

Here, if the number of pieces of treatment information on the tooth corresponding to the area is equal to or greater than a threshold value, the treatment information display device 100 displays the summary information on the display 101 to provide to the user with the same, and if the number is less than the threshold value, the treatment information display device 100 displays the detailed information on the display 101 to provide the user with the same. Further, in the case of receiving the user's selection for the summary information through the interface, the treatment information display device 100 displays the detailed information corresponding to the summary information selected by the user, thereby providing the user with the detailed information the user wants.

The summary information may be information obtained by statisticizing the past treatment information, the current treatment information, and the future treatment information of the tooth corresponding to the area. For example, the summary information may be displayed in an interface window in which the number of pieces of past treatment information, the number of pieces of current treatment information, and the number of pieces of future treatment information of a tooth are displayed in numbers. Further, the summary information may indicate the status of past treatment information, current treatment information, and future treatment information of the tooth, and may be displayed in a graph window including a pie graph or a bar graph as a method for representing a status result.

The display 101 may display a navigation bar for allowing selection from the time at which the treatment information is initially generated to the time at which the patient's treatment is expected to be completed. In this case, the treatment information display device 100 may receive selected time from the user through the navigation bar. Further, the treatment information display device 100 may select and display on the display 101 one of the past treatment information, the current treatment information, and the future treatment from the treatment information of the tooth corresponding to the area according to movement of the navigation bar and the position where the navigation bar stops moving to provide the user with treatment information corresponding to the time selected by the user.

Further, the treatment information display device 100 may search for a tooth for which treatment information was generated before the time corresponding to the position where the navigation bar stops moving. The treatment information display device 100 displays the color of the area or the area dividing line of the searched tooth, and the display effect to be applied to the area of the tooth to be differentiated from those of the area of an unsearched tooth, thereby allowing the user to recognize the tooth for which the treatment information is generated within the time section selected by the user.

The treatment information display device 100 may display a list of diagnosis types or treatment types. In this case, the treatment information display device 100 may receive the user's selection of a diagnosis type or a treatment type through the interface. The treatment information display device 100 may search for a tooth corresponding to the diagnosis type or treatment type selected by the user. Here, the treatment information display device 100 may display the color of the area or the area dividing line of the searched tooth, and the display effect to be applied to the area of the tooth to be differentiated from those of the area of the unsearched tooth, thereby allowing the user to recognize the tooth for which the treatment information of the diagnosis type or treatment type selected by the user is generated.

Here, in the case that the diagnosis type or treatment type selected by the user requires an image other than the image of teeth, the treatment information display device 100 may map the image corresponding to the diagnosis type or treatment type selected by the user to the image of teeth and display the same on the display 101.

Further, the treatment information display device 100 may request the display 101 to display a single image of a tooth corresponding to an area identified according to the user's selection. In this case, the treatment information display device 100 may receive a direction selected by the user on the image of the tooth through the interface. Then, according to the direction selected by the user, the treatment information display device 100 may select one of the past treatment information, the current treatment information, and the future treatment information of the tooth corresponding to the area, and an image relating to the tooth corresponding to the area and further display the same on the display 101.

The treatment information display device 100 may accumulate pieces of treatment information displayed on images of teeth of the patient generated at different times on one image of teeth and provide the same to the user.

First, the treatment information display device 100 may identify the most recently generated image of teeth from the patient's images of teeth generated at different times and display the same on the display 101. In addition, the treatment information display device 100 may display the area dividing lines on an image of teeth 102, each area dividing line for dividing an area of each of teeth included in the image of teeth displayed on the display 101.

Then, the treatment information display device 100 may receive the user's selection of any one of a plurality of areas divided according to the area dividing lines through the interface. In this case, the treatment information display device 100 may collect treatment information corresponding to the area corresponding to the user's selection from each of the patient's images of teeth generated at different times and provide the same to the user.

In this case, the treatment information display device 100 may display pieces of the treatment information collected from each of the patient's images of teeth generated at different times in an accumulated manner on the most recently generated image of teeth. If the number of the pieces of treatment information collected from each of the patient's images of teeth generated at different times is equal to or greater than a threshold value, the treatment information display device 100 may sort the collected pieces of treatment information in chronological order, and sequentially select and display a preset number of pieces of information of the sorted pieces of treatment information. Further, if the number of the pieces of treatment information collected from each of the patient's images of teeth generated at different times is equal to or greater than the threshold value, the treatment information display device 100 may display the summary information of the collected pieces of treatment information on the image of teeth 102.

The treatment information display device 100 may display the treatment information for each tooth in chronological order thereby providing the user with a treatment history of the tooth.

In addition, the treatment information display device 100 varies a method of displaying the treatment information according to an attribute of the treatment information, so that the user can easily recognize which attribute of a treatment result of the past, the current status of the tooth, and a treatment plan for the tooth the treatment information corresponds to.

Further, the treatment information display device 100 may prevent an unnecessarily large amount of treatment information from obscuring the image of teeth by maintaining the number of pieces of treatment information displayed on the image of teeth below a predetermined number.

Furthermore, the treatment information display device 100 may increase the number of pieces of treatment information displayed in the same area by decreasing the size of each piece of treatment information displayed on the image of teeth.

Figure 2:
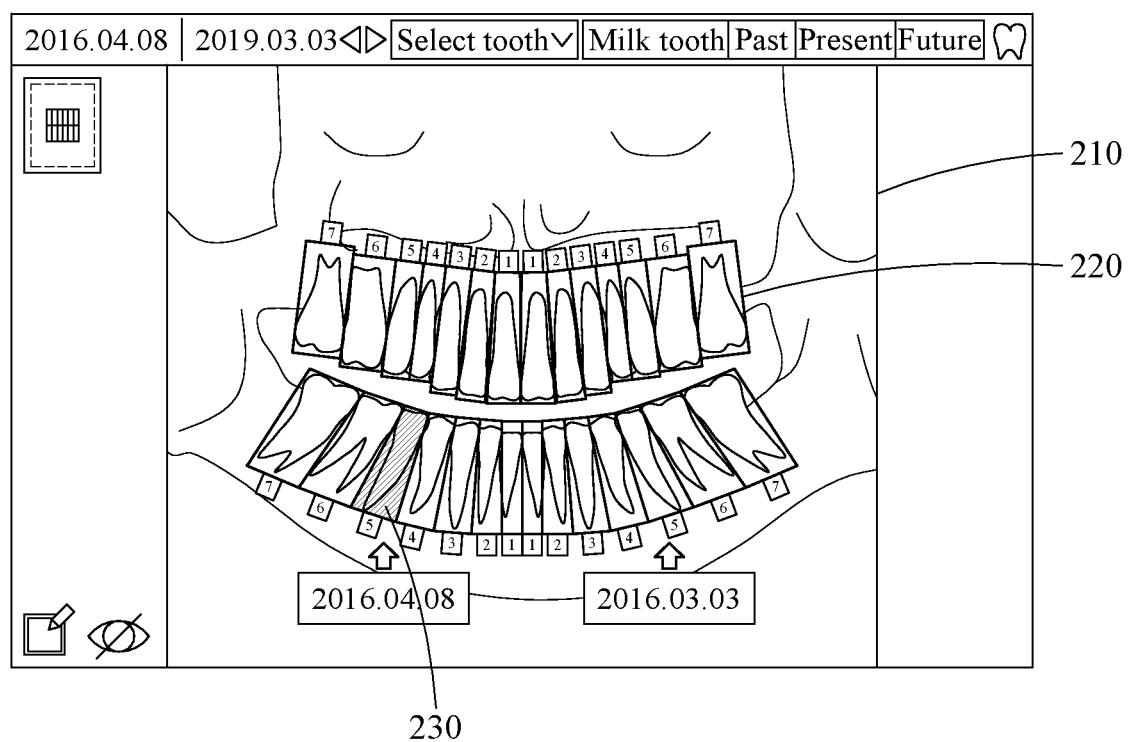
FIG. 2 is an example of a screen in which area dividing lines are displayed on an image of teeth according to an example embodiment.

FIG. 2 is an example of a screen in which the area dividing lines are displayed on an image of teeth according to an example embodiment.

As shown in FIG. 2, the treatment information display device 100 may overlap and display area dividing lines 220 on an image of teeth 210, each of the area dividing lines for dividing an area of each of the teeth included in the image of teeth 210. The area dividing line 220 may be indicated by a solid line as shown in FIG. 2. The area dividing line 220 may be indicated by a dotted line or a transparent line.

The treatment information display device 100 may provide the user with an interface for selecting at least one area of a plurality of areas divided by the area dividing lines 220.

In the case that the user selects an area 230 using the interface, the treatment information display device 100 may identify the area 230 selected via the interface. In this case, the treatment information display device 100 may provide the user with an input interface through which the user can input information in relation to the area 230. The treatment information display device 100 may store and manage the information input to the input interface as treatment information corresponding to the area 230. For example, the input interface may be a notepad or an application such as pen charting.

Figure 3:
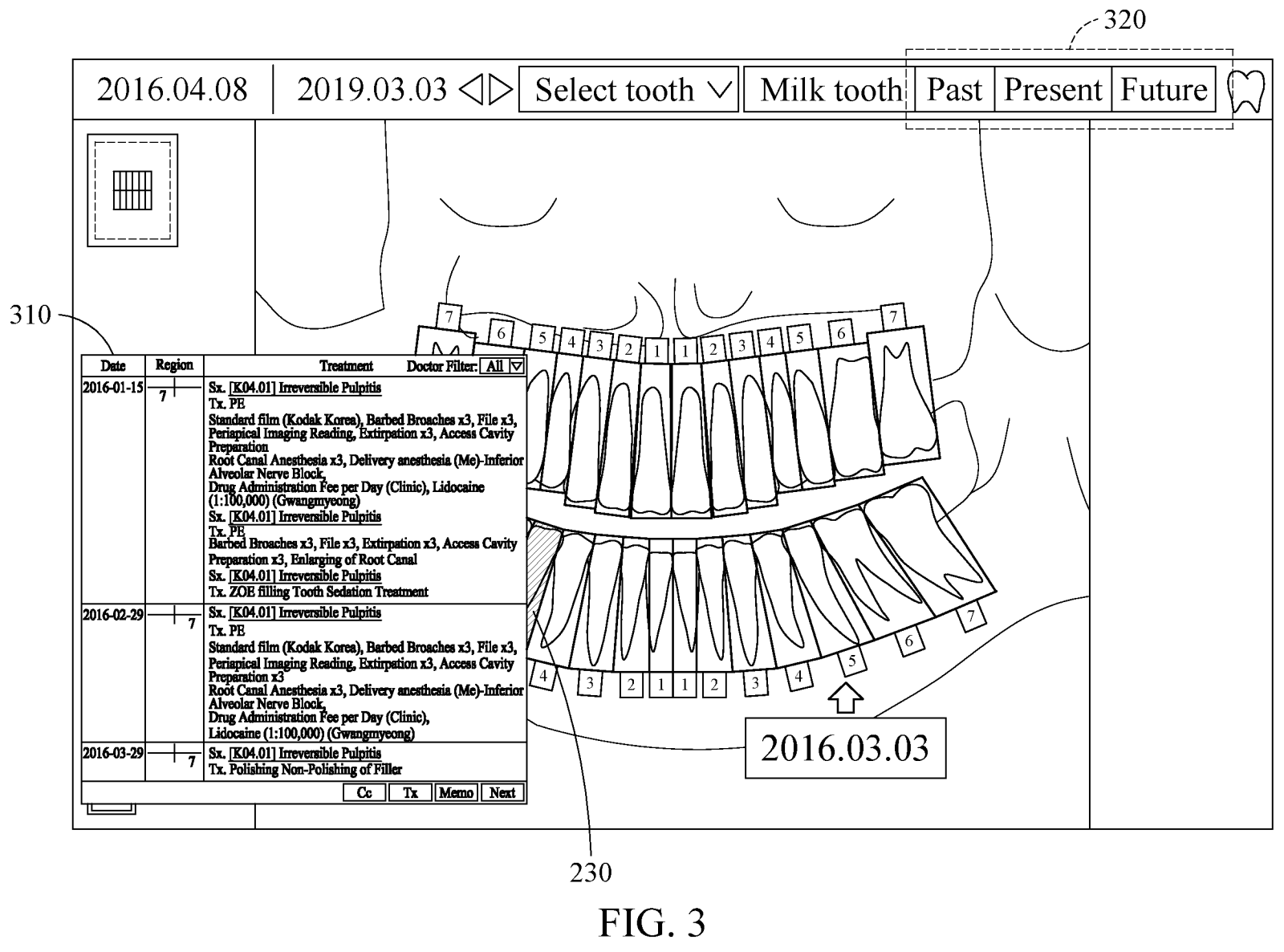

Then, the treatment information display device 100 may provide the user with pieces of treatment information 310 of the tooth corresponding to the identified area 230 as shown in FIG. 3.

In addition, the treatment information display device 100 may display an interface 320 for receiving time information selected by the user on the display 101.

In the case that the user selects the past in the interface 320, the treatment information display device 100 may display only the past treatment information of the pieces of treatment information 310 of the tooth corresponding to the area 230 on the display 101. In the case that the user selects the present in the interface 320, the treatment information display device 100 may display only the current treatment information of the pieces of treatment information 310 of the tooth corresponding to the area 230 on the display 101. In the case that the user selects the future on the interface 320, the treatment information display device 100 may display only the future treatment information of the pieces of treatment information 310 of the tooth corresponding to the area 230 on the display 101.

The interface 320 may receive a plurality of different time sections selected by the user. For example, in the case that the user selects the past and the future on the interface 320, the treatment information display device 100 may display the past treatment information and the future treatment information of the pieces of treatment information 310 of the tooth corresponding to the area 230 on the display 101.

The treatment information 310 displayed on the display 101 in FIG. 3 may be the detailed information. If the number of the pieces of treatment information of the tooth corresponding to the area 230 is equal to or greater than a threshold value, or according to the user's request, the treatment information display device 100 may display the summary information of pieces of treatment information 410 as shown in FIG. 4 on the display 101.

Since the detailed information includes the date on which the treatment information was generated, the name of treatment, and a specific prescription for the treatment, only three pieces of treatment information 310 can be displayed at a time as shown in FIG. 3.

Figure 4:
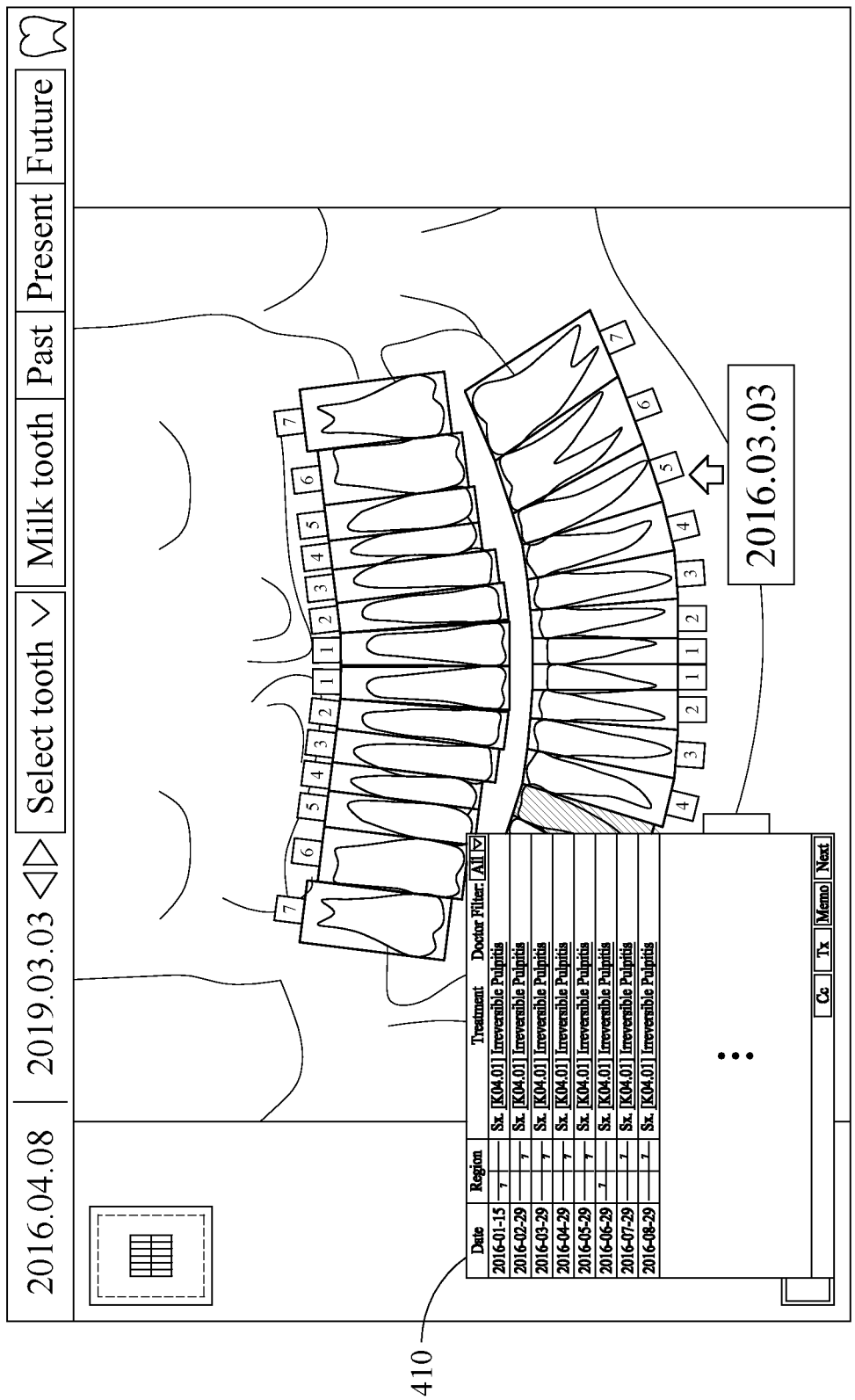
FIG. 4 is an example of a screen in which treatment information is displayed according to another example embodiment.

On the other hand, since the summary information includes only the date on which the treatment information was generated and the name of the treatment, nine or more pieces of treatment information 410 may be displayed as shown in FIG. 4.

Accordingly, by requesting the treatment information display device 100 to display the summary information, the user can easily check the number of pieces of treatment information on the tooth and treatment dates.

In addition, the treatment information display device 100 may provide the user with an interface for selecting the summary information, and in the case that the user selects one of pieces of summary information, display the detailed information corresponding to the selected summary information, thereby allowing the user to recognize the detailed information.

Figure 5:
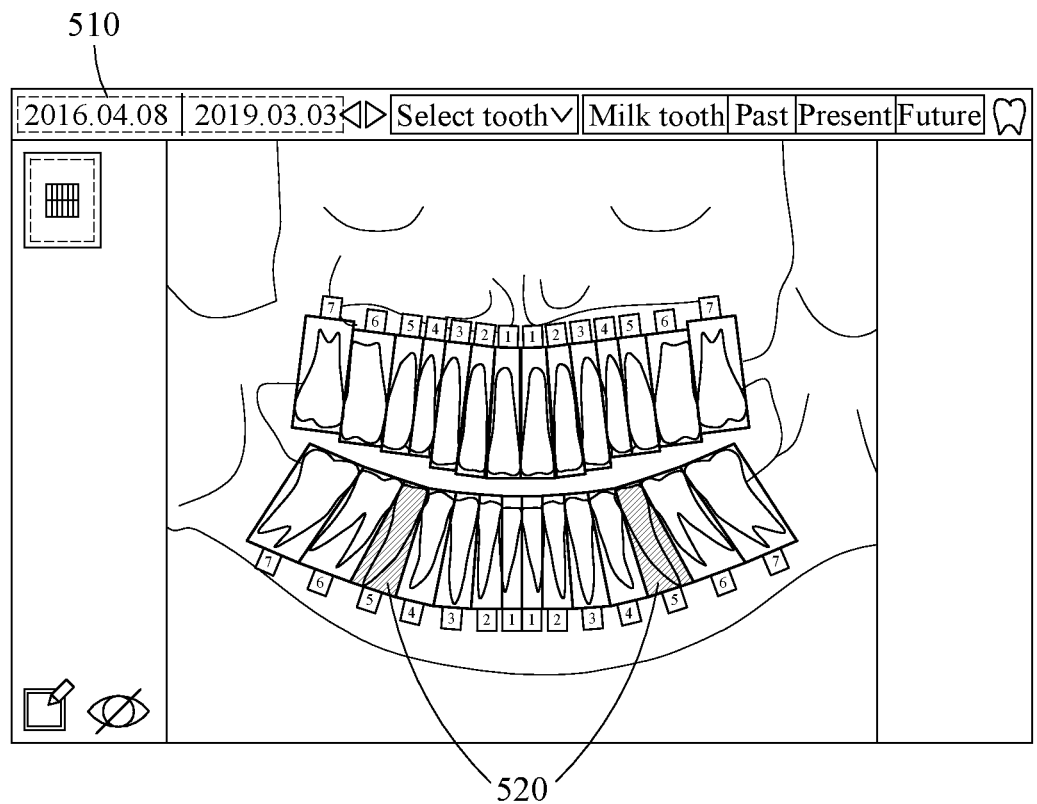
FIG. 5 is an example of a screen in which teeth for which treatment information is generated for a specific time section are displayed according to an example embodiment.

FIG. 5 is an example of a screen in which a tooth on which treatment information is generated in a specific time section is displayed according to an example embodiment.

The treatment information display device 100 may receive an input of a time section selected by the user through an interface 510 for selecting a time section. The treatment information display device 100 may search for a tooth for which the treatment information is generated within the time section input to the interface 510. For example, as shown in FIG. 5, the treatment information display device 100 may search for teeth for which the treatment information was generated between Apr. 8, 2016 and Mar. 3, 2019.

Then, the treatment information display device 100 may display the areas of searched teeth 520 to be differentiated from those of unsearched teeth so that the user can easily recognize the teeth for which the treatment information was generated within the time section. For example, the treatment information display device 100 may hatch the areas of the searched teeth 520 as shown in FIG. 5, thereby allowing the user to identify the teeth for which the treatment information was generated between Apr. 8, 2016 and Mar. 3, 2019.

The interface 510 may be configured so that the user manually inputs the start time and the end time of the time section. Alternately, the interface 510 may be configured to automatically set the present, the time at which the image of teeth is displayed, as the start time or end time of the time section. Alternately, the interface 510 may automatically sets a preset previous time based on the present (e.g., one week ago) as the end time of the time section, or automatically set a preset time section (e.g., one week after the present). The preset time section may be a time section set in relation to the treatment. For example, from the time at which the orthodontic treatment starts to the time at which an intermediate state can be checked according to the orthodontic schedule may be set as the preset time section.

Figure 6:
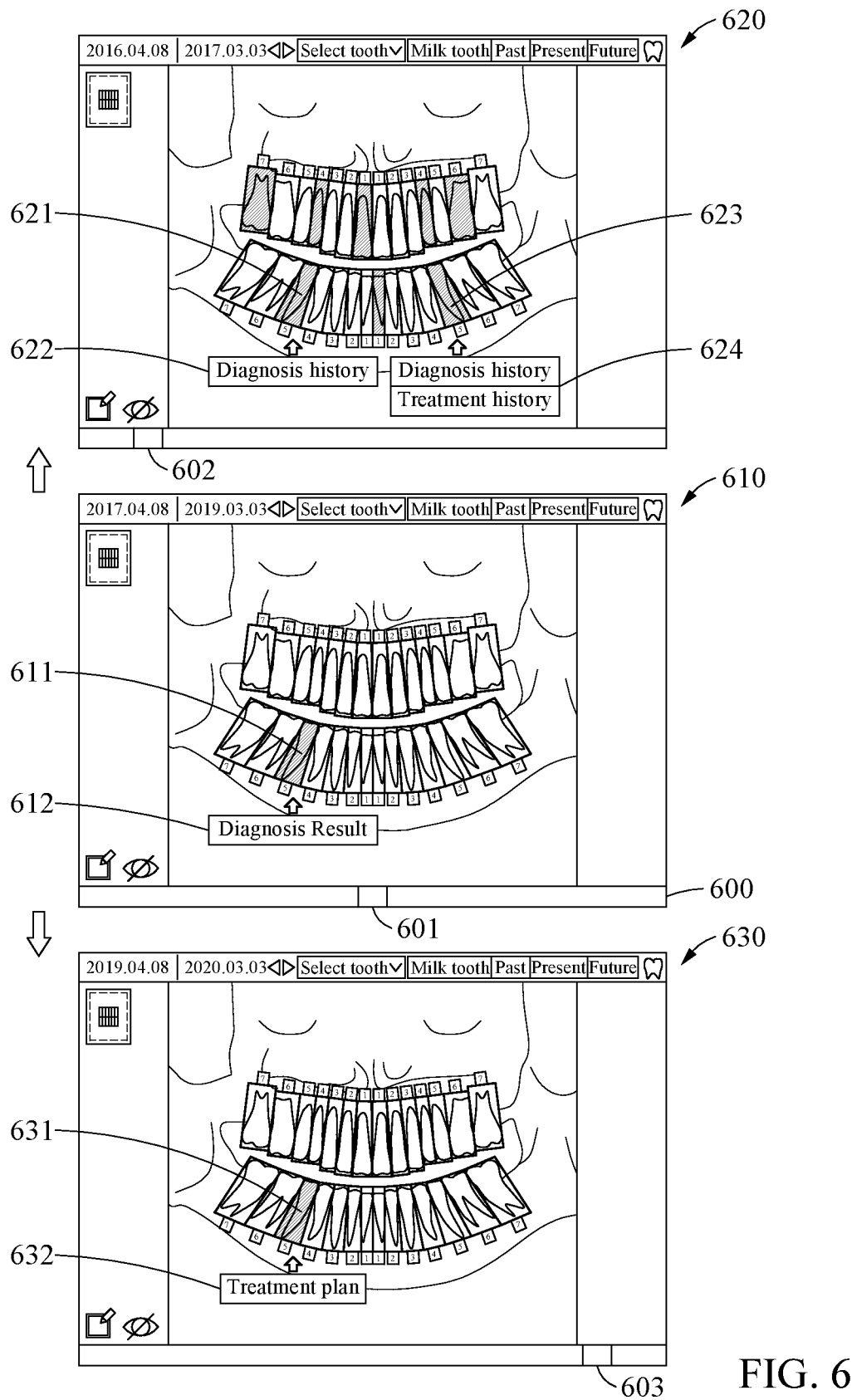
FIG. 6 is an example of a process of changing treatment information using a navigation bar according to an example embodiment.

FIG. 6 is an example of a process of changing treatment information using a navigation bar according to an example embodiment.

The display 101 may display a navigation bar 600 for allowing selection from a time at which the treatment information is initially generated to a time at which the patient's treatment is expected to be completed.

In this case, the time at which the treatment of the patient is expected to be completed may be determined according to the diagnosis result of the patient, or may be determined as a time having an interval of a predetermined period of time or more, such as one year or two years. Further, the treatment information display device 100 may adaptively change the completion time of the orthodontic treatment according to the treatment information input during the process of the patient's orthodontic treatment, and change the range of the navigation bar 600 according to the changed orthodontic treatment completion time. For example, in the case that it is expected that the orthodontic treatment will take 6 months, the maximum value of the navigation bar 600 may be a time 6 months after the current time. However, the patient's orthodontic treatment may be delayed, and the orthodontic treatment may not be completed even after 6 months. In this case, the treatment information display device 100 may change the maximum value of the navigation bar 600 to a later time after six months according to the treatment information input during the patient's orthodontic process. In addition, in the case that the patient's treatment progress is better than expected, the time for orthodontic completion may be shortened. In this case, the treatment information display device 100 may change the maximum value of the navigation bar 600 to a time between the current time and six months after the current time according to the treatment information input during the patient's orthodontic process.

A screen 610 may be a screen when the navigation bar 600 is in a default state. Since the treatment information may be classified into past treatment information, current treatment information, and future treatment information based on the time at which the image of teeth 102 is displayed, the navigation bar 600 in the default state may also be located in the center 601 corresponding to the current treatment information, which is the reference time. Here, the treatment information display device 100 may display an area of a tooth 611 for which a diagnosis result, which is current treatment information 612, is generated differently from areas of other teeth, and display the current treatment information 612 so as to match the same to the area 611.

A screen 620 may be a screen in which the user moves the navigation bar 600 to the left. In this case, the treatment information display device 100 may identify a past time corresponding to a position where the navigation bar stops moving. Then, the treatment display device 100 may display areas of teeth 621 and 623 in which past treatment information corresponding to the identified past time was generated differently from areas of other teeth. In addition, the treatment information display device 100 may display the areas of teeth 621 and 623 to be differentiated from the area 611 of the screen 610 to indicate that they are teeth corresponding to the past treatment information.

Depending on the condition of a tooth, in the case there is a damage to the extent that no treatment is required, only diagnosis may be performed and treatment may not be performed. In the case that the damage to the teeth is above a certain level, diagnosis and treatment based on the diagnosis may be performed. Accordingly, as shown in FIG. 6, the treatment information display device 100 may display past treatment information 622 including a diagnosis history so as to match the same to the area of the tooth 621 for which only diagnosis has been performed, and display past treatment information 625 including both a diagnosis history and a treatment history so as to match the same to the area of the tooth 623 for which both diagnosis and treatment have been performed.

A screen 630 may be a screen in which the user moves the navigation bar 600 to the right. In this case, the treatment information display device 100 may identify a future time corresponding to a position where the navigation bar stops moving. Then, the treatment display device 100 may search for future treatment information 632 including a treatment plan corresponding to the identified future time. In this case, the treatment display device 100 may display an area 631 of a tooth corresponding to the searched future treatment information differently from other areas of teeth, and display the future treatment information 632 so as to match the same to the area 631. In addition, the treatment information display device 100 may display the area 631 of the tooth to be differentiated from the area 611 of the screen 610 and the areas 621 and 623 of the screen 620 to show that the tooth corresponds to the future treatment information.

The treatment information display device 100 may show a process in which teeth are changed in a panoramic image according to the movement of the navigation bar as an animation-like effect.

Figure 7:
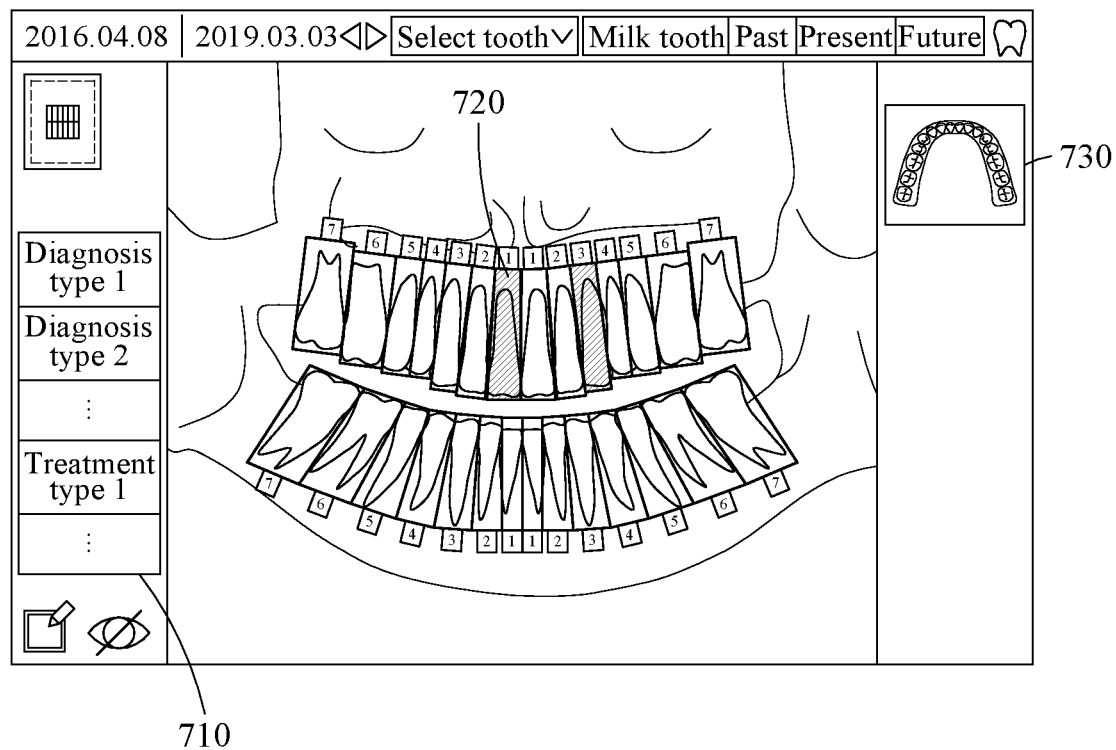
FIG. 7 is an example of a screen in which a tooth for which treatment information corresponding to a diagnosis type or a treatment type is generated is displayed according to an example embodiment.

FIG. 7 is an example of a screen in which a tooth for which treatment information corresponding to a diagnosis type or a treatment type is generated is displayed according to an example embodiment.

The treatment information display device 100 may display a list of diagnosis types and treatment types 710. In this case, the treatment information display device 100 may receive a selection of a diagnosis type or a treatment type included in the list 710 from the user. For example, diagnosis type 1 and diagnosis type 2 may be "caries" and "fracture", respectively. In addition, treatment type 1 and treatment type 2 may be "inlay treatment" or "resin treatment", respectively.

The treatment information display device 100 may search for a tooth corresponding to the diagnosis type or treatment type selected by the user. Here, the treatment information display device 100 may display the color of an area 720 of the searched tooth or the color of the area dividing line, and the display effect to be applied to the area of the tooth to be differentiated from those of areas of unsearched teeth, so that the user can recognize the tooth for which treatment information of the diagnosis type or treatment type selected by the user is generated.

In the case that the diagnosis type or treatment type selected by the user requires an image other than the image of teeth, the treatment information display device 100 may map an image 730 corresponding to the diagnosis type or treatment type selected by the user to the image of teeth and display the same on the display 101, as shown in FIG. 7. For example, the image 730 may be one of a panoramic image, a periapical image, a CT, a head radiation, and a scan.

Figure 8:
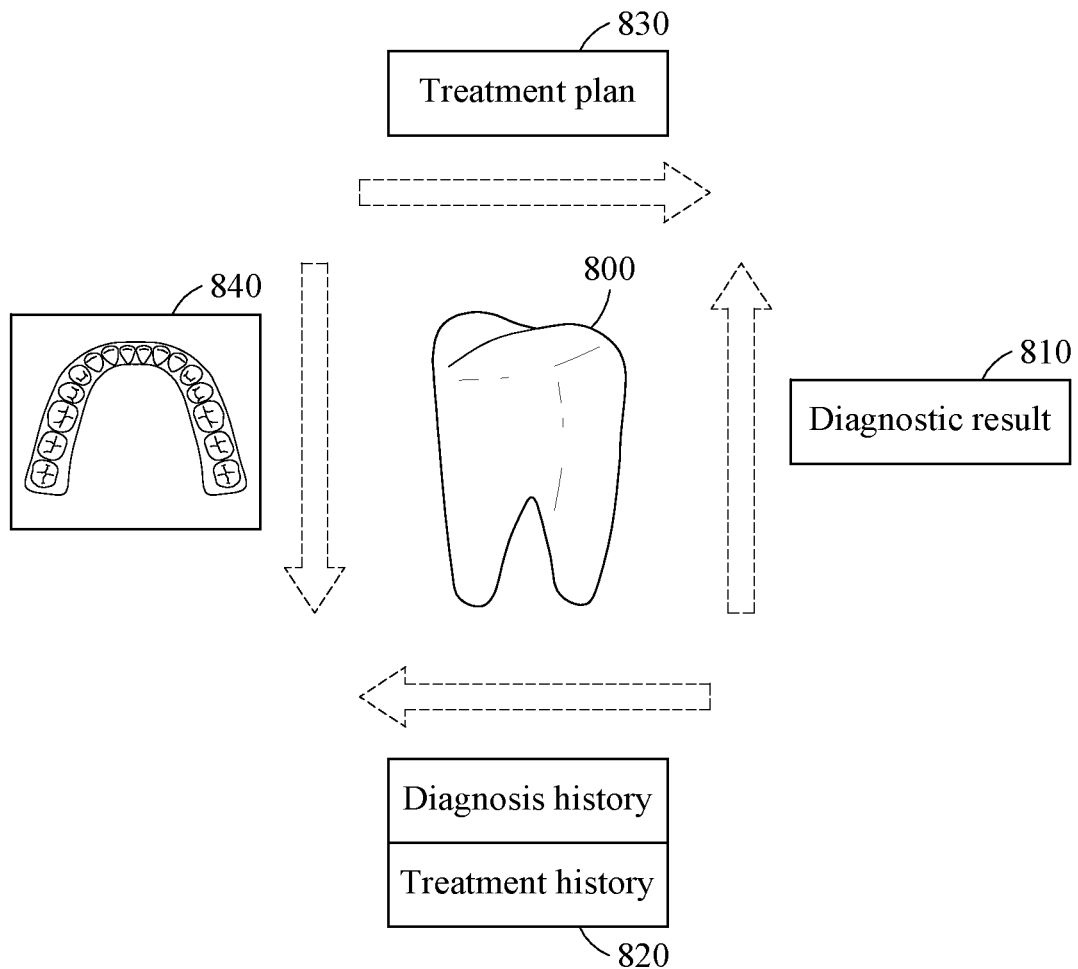
FIG. 8 is an example of operations of a method for providing different information according to a user's manipulation according to an example embodiment.

FIG. 8 is an example of operations of a method for providing different information according to the user's manipulation according to an example embodiment.

The treatment information display device 100 may display an image of a tooth 800 corresponding to an area identified according to the user's selection, as shown in FIG. 8.

In this case, the treatment information display device 100 may receive a direction selected by the user on the image of the tooth 800 through the interface. Then, according to the direction selected by the user, the treatment information display device 100 may select and display further one of past treatment information, current treatment information, and future treatment information of the tooth corresponding to the area, and images related to the tooth on the display 101.

For example, as shown in FIG. 8, in the case that the user drags the image of the tooth 800 upward, the treatment information display device 100 may display a diagnosis result 810 that is the current treatment information so as to match the same to the image of the tooth 800.

In the case that the user drags the image of the tooth 800 to the left, the treatment information display device 100 may display a diagnosis history and a treatment history 820, which are the past treatment information, so as to match the same to the image of the tooth 800.

In the case that the user drags the image of the tooth 800 to the right, the treatment information display device 100 may display a treatment plan 830, which is the future treatment information, so as to match the same to the image of the tooth 800.

In the case that the user drags the image of the tooth 800 downward, the treatment information display device 100 may display an image 840 related to the tooth so as to match the same to the image of the tooth 800.

Here, the direction selected by the user and information corresponding thereto may be changed according to an example embodiment. For example, in another example embodiment, in response to the user dragging the image of the tooth 800 to the right, the treatment information display device 100 may display the diagnosis result 810 or display the image 840 related to the tooth.

Figure 9:
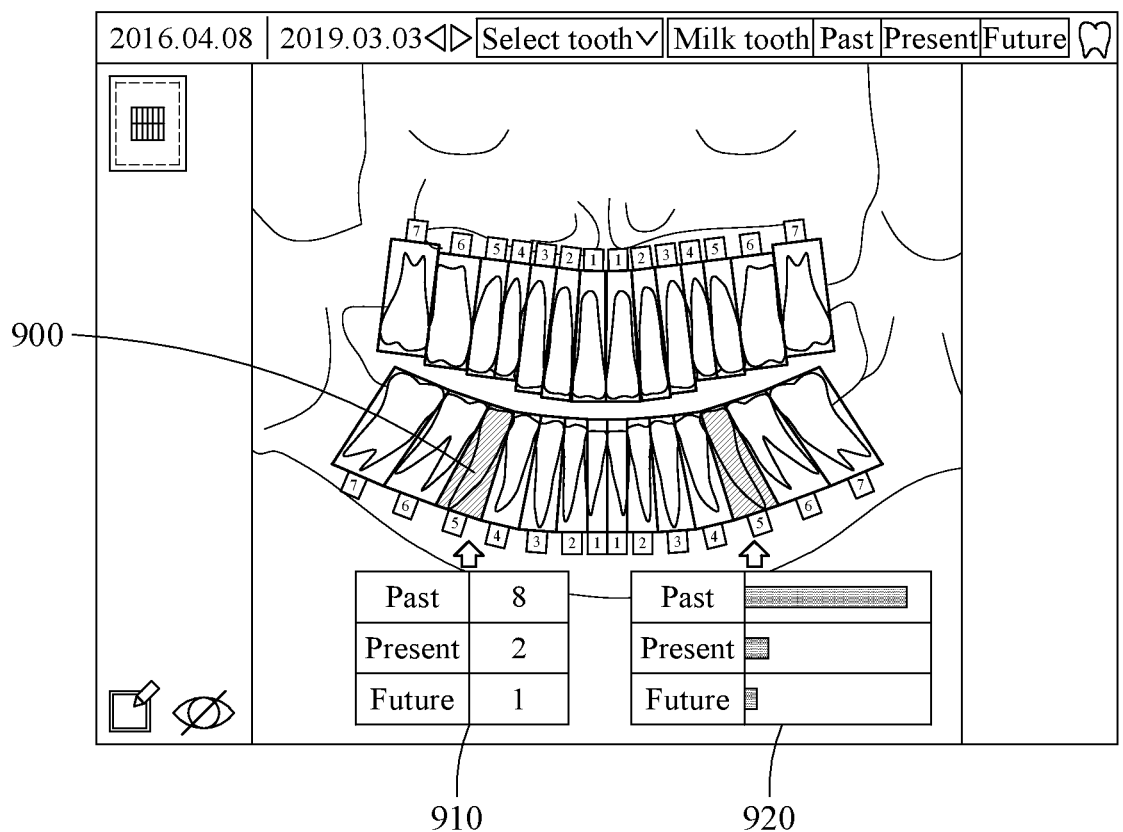
FIG. 9 is an example of a screen in which statistical summary information is displayed according to an example embodiment.

FIG. 9 is an example of a screen in which statistical summary information is displayed according to an example embodiment.

The treatment information display device 100 may statisticize past treatment information, current treatment information, and future treatment information of each tooth. In addition, in the case that the user selects an area of a tooth 900, the treatment information display device 100 may display summary information obtained by statisticizing the past treatment information, the current treatment information, and the future treatment information of the tooth so as to match the same to the area of the tooth 900. For example, the summary information may be displayed as an interface window 910 in which each of the number of pieces of past treatment information, the number of pieces of current treatment information, and the number of pieces of future treatment information of the tooth is displayed in numbers. In addition, the summary information may be displayed as a graph window 920 in which the states of the past treatment information, the current treatment information, and the future treatment information of the tooth are displayed as a pie graph or a bar graph, respectively.

In the case that the user selects one of the past, present, and future from the summary information, the treatment information display device 100 may display one of the past treatment information, the current treatment information, and the future treatment information of the tooth according to the user's selection. For example, in the case that the user selects the past from the summary information, the treatment information display device 100 may display the past treatment information. In the case that the user selects the present from the summary information, the treatment information display device 100 may display the current treatment information. In the case that the user selects the future from the summary information, the treatment information display device 100 may display the future treatment information.

In this case, the treatment information display device 100 may display a list of pieces of treatment information classified into past treatment information, current treatment information, or future treatment information of the tooth. In this case, as shown in FIG. 4, only the date on which the treatment information was generated and the name of the treatment may be displayed in the list of pieces of treatment information. In the case that the user selects one of the pieces of treatment information included in the list, the treatment information display device 100 may display details of the treatment information selected by the user.

In the case that the user selects one of the past, present, and future from the summary information, the treatment information display device 100 may display details of pieces of treatment information corresponding to the user's selection of the past treatment information, current treatment information, and future treatment information of the tooth, as shown in FIG. 3.

Figure 10:
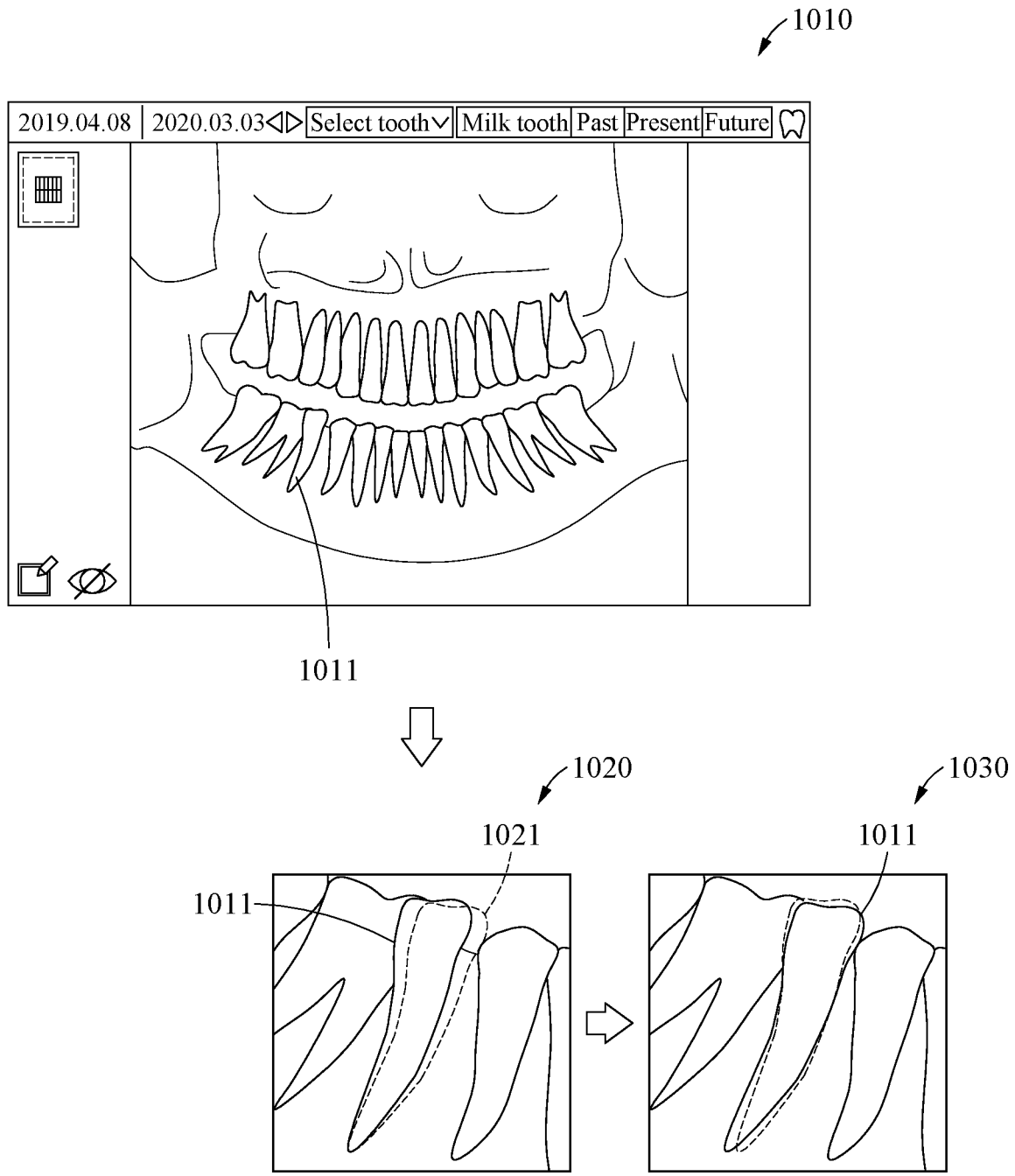
FIG. 10 is an example of a screen in which an image of teeth is converted into an animation image according to an example embodiment.

FIG. 10 is an example of a screen in which an image of teeth is converted into an animation image according to an example embodiment.

At step 1010, the treatment information display device 100 may receive the user's selection of any one of a plurality of areas divided according to the area dividing lines through the interface to identify a tooth 1011 selected by the user.

At step 1020, the treatment information display device 100 may enlarge and display a screen of the tooth 1011. In this case, the treatment information display device 100 may display the screen of the tooth 1011 in place of the image of the teeth 102 on the display 101, as shown in FIG. 10. Further, the treatment information display device 100 may reduce the image of teeth 102 and divide the screen of the display 101 to display the screen of the tooth 1011 together with the image of teeth 102.

In addition, the treatment information display device 100 may identify a position, an angle, or a shape 1021 to which the tooth 1011 is to be corrected according to a treatment plan of the future treatment information.

At step 1030, the treatment information display device 100 may display an animation image in which a process of the tooth 1011 changing from the current state to the position, angle, or shape 1021 to which the tooth 1011 is to be corrected is animated.

Figure 11:
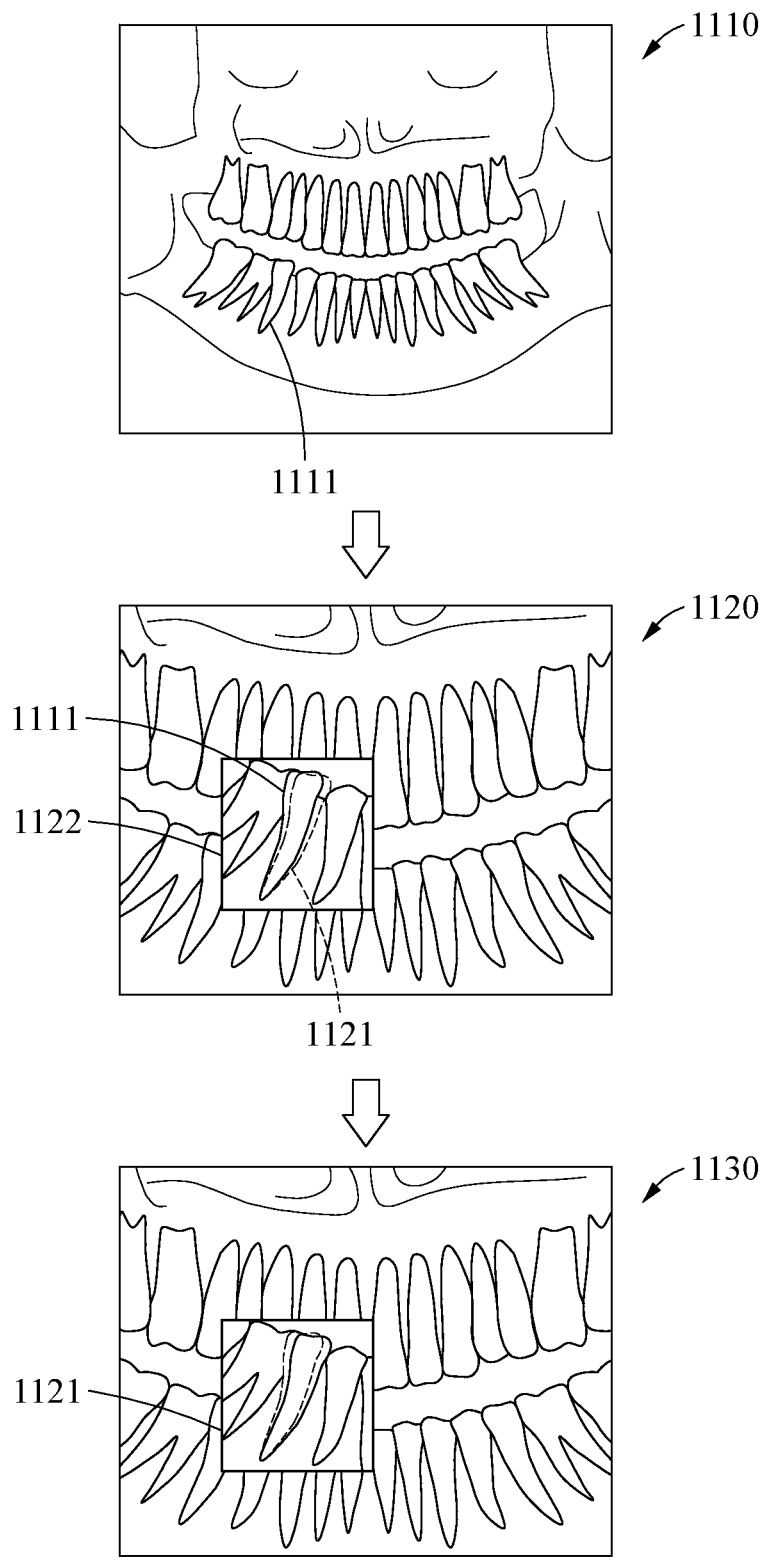
FIG. 11 is an example of a screen displaying an animation image overlapping an image of teeth according to an example embodiment.

FIG. 11 is an example of a screen displaying an animation image overlapping an image of teeth according to an example embodiment.

At step 1110, the treatment information display device 100 may receive the user's selection of any one of a plurality of areas divided according to the area dividing lines through the interface to identify a tooth 1111 selected by the user.

At step 1120, the treatment information display device 100 may overlap and display a screen of the tooth 1011 on the image of teeth 102. In addition, the treatment information display device 100 may identify a position, an angle, or a shape 1121 to which the tooth 1111 is to be corrected according to a treatment plan of the future treatment information.

At step 1130, the treatment information display device 100 may display an animation image in which a process of the tooth 1111 changing from the current state to the position, angle, or shape 1121 to which the tooth 1111 is to be corrected is animated.

Figure 12:
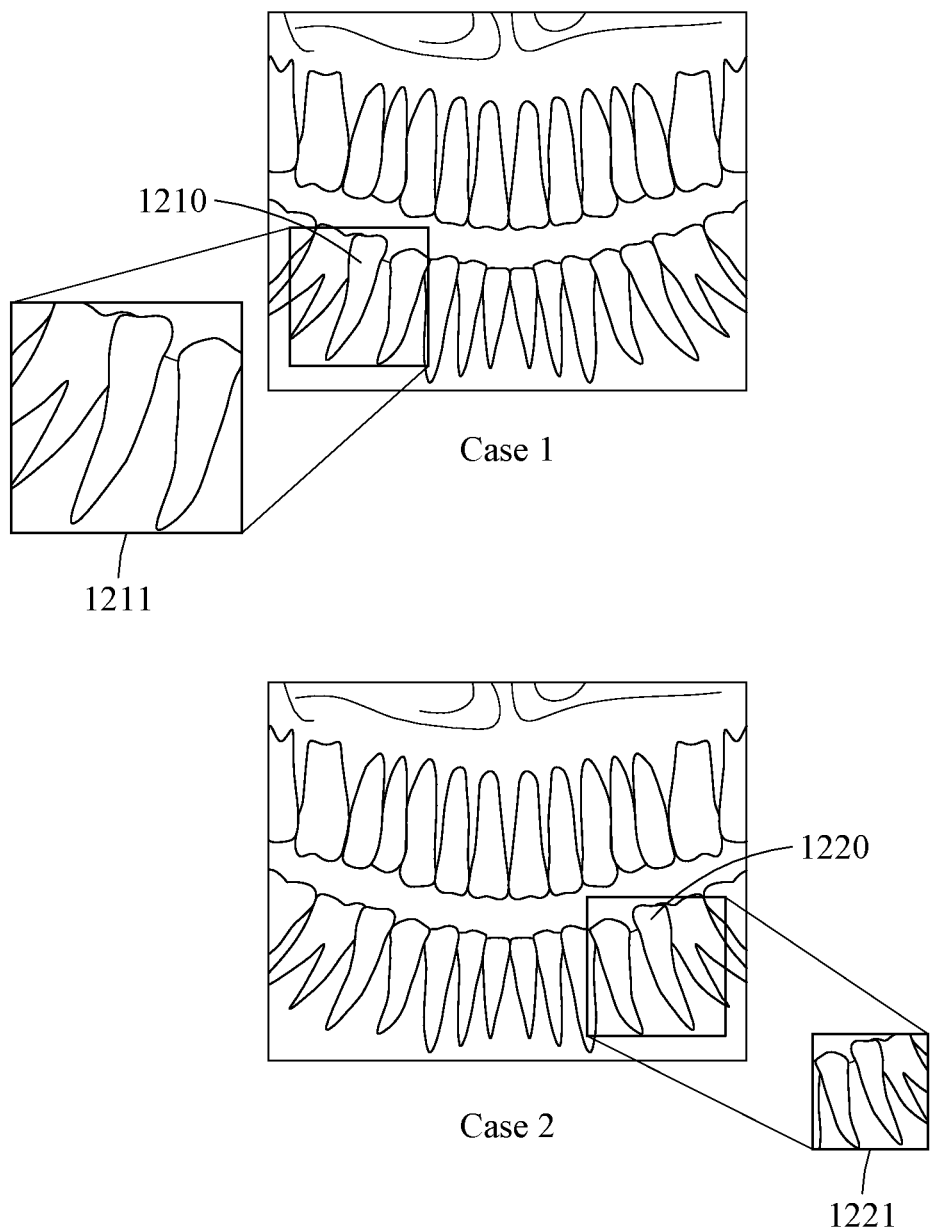
FIG. 12 is an example of a screen displaying different sizes of animation images according to the number of pieces of treatment information according to an example embodiment.

FIG. 12 is an example of a screen displaying different sizes of animation images according to the number of pieces of treatment information according to an example embodiment.

The sum of the number of pieces of past treatment information, the number of pieces of current treatment information, and the number of pieces of future treatment information of a tooth 1210 may be 8, and the sum of the number of pieces of past treatment information, the number of pieces of current treatment information, and the number of pieces of future treatment information of a tooth 1220 may be 8.

In the case that the tooth 1210 is identified as a tooth selected by the user, the treatment information display device 100 may display a screen 1211 of the tooth 1210 as shown in Case 1 of FIG. 12. In this case, the screen 1211 of the tooth 1210 may be displayed as shown in FIG. 10 or FIG. 11.

Alternately, in the case that the tooth 1220 is identified as the tooth selected by the user, the treatment information display device 100 may display a screen 1221 of the tooth 1220 as shown in Case 2 of FIG. 12. In this case, the screen 1221 of the tooth 1220 may be displayed as shown in FIG. 10 or FIG. 11.

The size of the screen 1211 of the tooth 1210 and the size of the screen 1221 of the tooth 1220 may be determined according to the number of the pieces of treatment information. Since the number of the pieces of treatment information of the tooth 1210 is greater than the number of the pieces of treatment information of the tooth 1220, the screen 1211 of the tooth 1210 may be displayed larger than the screen 1221 of the tooth 1220 as shown in FIG. 12.

In other words, the treatment information display device 100 may determine the size of the tooth screen in proportion to the number of the pieces of treatment information, so that the user can easily recognize whether the number of pieces of treatment information on the tooth is large or small through the size of the screen of the tooth.

Figure 13:
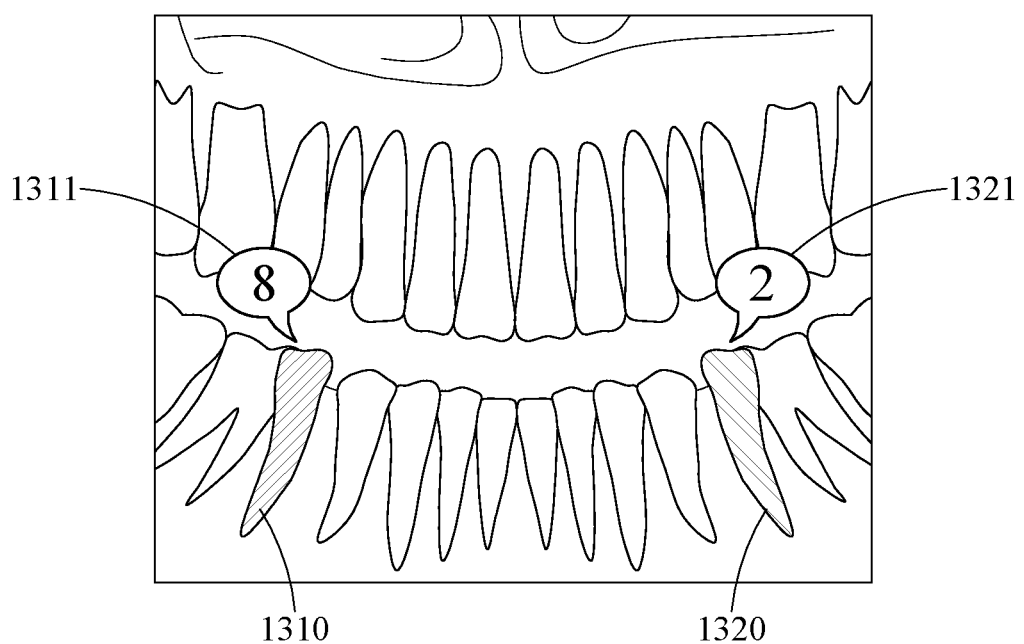
FIG. 13 is an example of a screen for displaying areas of teeth differentiated according to the number of pieces of treatment information according to an example embodiment.

FIG. 13 is an example of a screen for displaying areas of teeth differentiated according to the number of pieces of treatment information according to an example embodiment.

The sum of the number of pieces of past treatment information, the number of pieces of current treatment information, and the number of pieces of future treatment information of a tooth 1310 may be 8, and the sum of the number of pieces of past treatment information, the number of pieces of current treatment information, and the number of pieces of future treatment information of a tooth 1320 may be 8.

The treatment information display device 100 may display the tooth 1310 and the tooth 1320 differently. For example, as shown in FIG. 13, by applying the hatching effect to the tooth 1310, which has a larger number of pieces of treatment information than the tooth 1320, stronger than the tooth 1320, it is possible to enable the user to easily recognize whether the number of pieces of treatment information of the tooth is large or small through the degree of hatching.

It is an example embodiment that the treatment information display device 100 differently displays the tooth 1310 and the tooth 1320 using the hatching effect, and the treatment information display device 100 may display that the number of pieces of treatment information of the tooth 1310 is greater than the number of pieces of treatment information of the tooth 1320 through contrast, color, marker, symbol, and other effects. For example, the treatment information display device 100 may display the color of the tooth closer to red as the number of pieces of treatment information increases, and the color of the tooth closer to green as the number of treatment information decreases.

Further, as shown in FIG. 13, the treatment information display device 100 may map the numbers of pieces of treatment information 1311 and 1321 to the teeth 1310 and 1320, respectively, and display the same, thereby intuitively providing the user with the number of pieces of treatment information.

Figure 14:
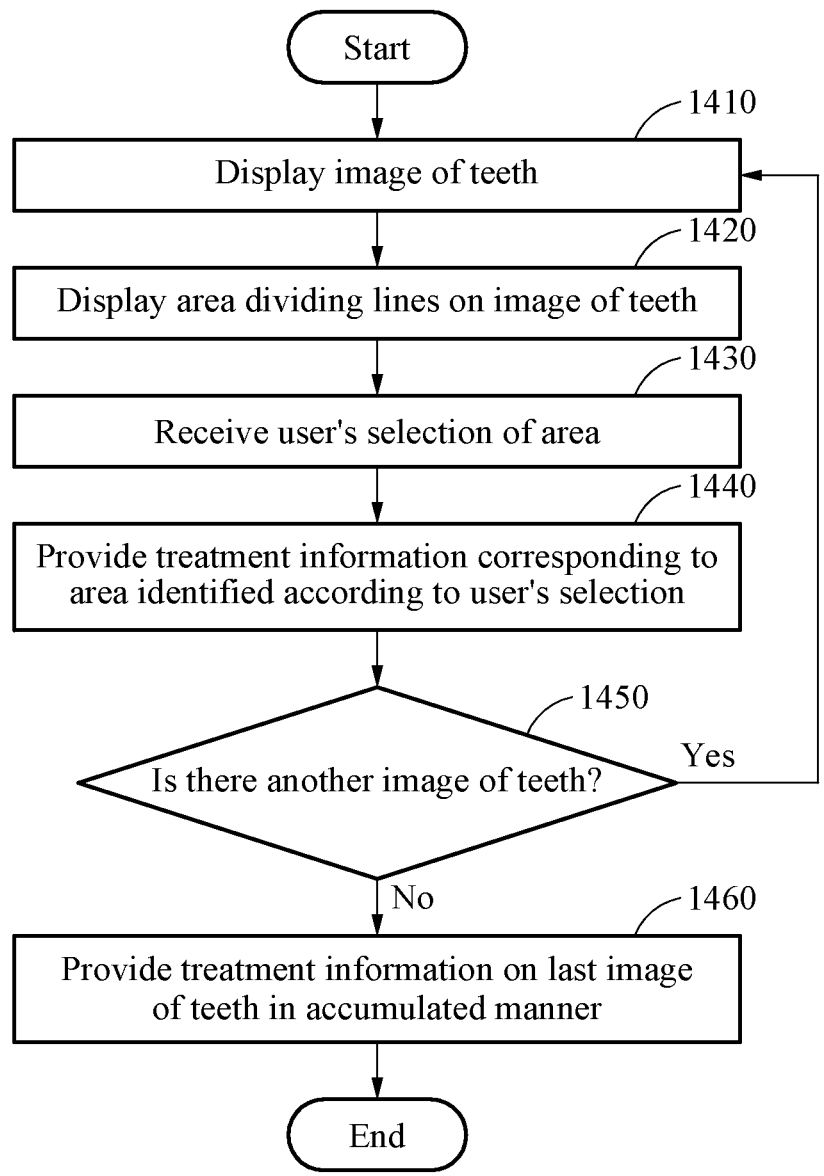
FIG. 14 is a flowchart illustrating a treatment information display method according to an example embodiment.

FIG. 14 is a flowchart illustrating a treatment information display method according to an example embodiment.

At step 1410, the treatment information display device 100 may display the patient's image of teeth 102 on the display 101.

At step 1420, the treatment information display device 100 may display the area dividing lines, each for dividing an area of each of the teeth included in the image of teeth 102, on the image of teeth 102 displayed at step 1410. Here, the treatment information display device 100 may receive the time information selected by the user through the interface. Further, the treatment information display device 100 may search for a tooth for which treatment information is generated within a time section included in the time information. Then, the treatment information display device 100 may display the area of the searched tooth to be differentiated from the areas of the unsearched teeth.

The treatment information display device 100 may receive time selected by the user through the navigation bar for allowing selection from the time at which the treatment information is initially generated to the time at which the patient's treatment is expected to be completed. Further, the treatment information display device 100 may search for a tooth for which the treatment information is generated before the time corresponding to the position where the navigation bar stops moving. In this case, the treatment information display device 100 may display the color of the area of the searched tooth or the color of the area dividing line, and the display effect to be applied to the area of the tooth to be differentiated from those of the areas of the unsearched teeth.

At step 1430, the treatment information display device 100 may receive the user's selection of any one of the plurality of areas divided according to the area dividing lines through the interface.

At step 1440, the treatment information display device 100 may provide the user with the treatment information on the tooth corresponding to the area identified according to the user's selection. For example, the treatment information display device 100 may map pieces of treatment information corresponding to the time information received from the user of piece of treatment information of the tooth corresponding to the area to an area corresponding to the user's selection and display the same. In addition, the treatment information display device 100 may sort the pieces of treatment information of the tooth corresponding to the area in chronological order, and sequentially select and display a preset number of pieces of information of the sorted pieces of treatment information.

In this case, the treatment information display device 100 may receive time selected by the user through the navigation bar for allowing selection from the time at which the treatment information is initially generated to the time at which the patient's treatment is expected to be completed. Then, the treatment information display device 100 may select and display one of the past treatment information, the current treatment information, and the future treatment information of the treatment information corresponding to the area according to the movement of the navigation bar and the position where the navigation bar stops moving.

Here, the treatment information display device 100 may display a list of diagnosis types or treatment types. Further, the treatment information display device 100 may receive the user's selection of a diagnosis type or a treatment type through the interface. Then, the treatment information display device 100 may search for a tooth corresponding to the diagnosis type or treatment type selected by the user. Next, the treatment information display device 100 may display the color of the area of the searched tooth or the color of the area dividing line, and the display effect to be applied to the area of the tooth to be differentiated from those of the area of the unsearched tooth. In the case that the diagnosis type or treatment type selected by the user requires an image other than the image of teeth, the treatment information display device 100 may map an image corresponding to the diagnosis type or treatment type selected by the user to the image of teeth and display the same.

Further, the treatment information display device 100 may display an image of a tooth corresponding to the area identified according to the user's selection. The treatment information display device 100 may receive a direction selected by the user on the image of the tooth through the interface. In this case, according to the direction selected by the user, the treatment information display device 100 may select and further display one of the past treatment information, the current treatment information, and the future treatment information of the tooth corresponding to the area, and an image related to the tooth corresponding to the area.

In addition, the treatment information display device 100 may display the summary information obtained by statisticizing the past treatment information, the current treatment information, and the future treatment information of the tooth corresponding to the area. In the case of receiving the user's selection for the summary information through the interface, the treatment information display device 100 may display one of a list of pieces of the past treatment information, a list of pieces of the current treatment information, and a list of pieces of the future treatment information according to the user's selection. Further, in the case that one of the pieces of treatment information included in the list is selected by the user, the treatment information display device 100 may display the detailed information on the piece of treatment information selected by the user.

At step 1450, the treatment information display device 100 may determine whether there is an image of teeth which is generated at a different time from the image of teeth displayed at step 1410 and for which treatment information is not displayed.

In the case that there is an image of teeth which is generated at a different time and for which treatment information is not displayed, the treatment information display device 100 may perform step 1410 again, and display the treatment information on an area selected by the user of the patient's image of teeth generated at the different time on the image of teeth.

In the case that no images of teeth generated at different times do not exist or the treatment information is displayed on all images of teeth generated at different times, the treatment information display device 100 may perform step 1450.

At step 1450, the treatment information display device 100 may provide the user with pieces of the treatment information displayed in each of the patient's images of teeth generated at different times on one image of teeth in an accumulated manner. In this case, in the case that no images of teeth generated at different times exist, the treatment information display device 100 may maintain the treatment information displayed on the tooth information at step 1440.

Figure 15:
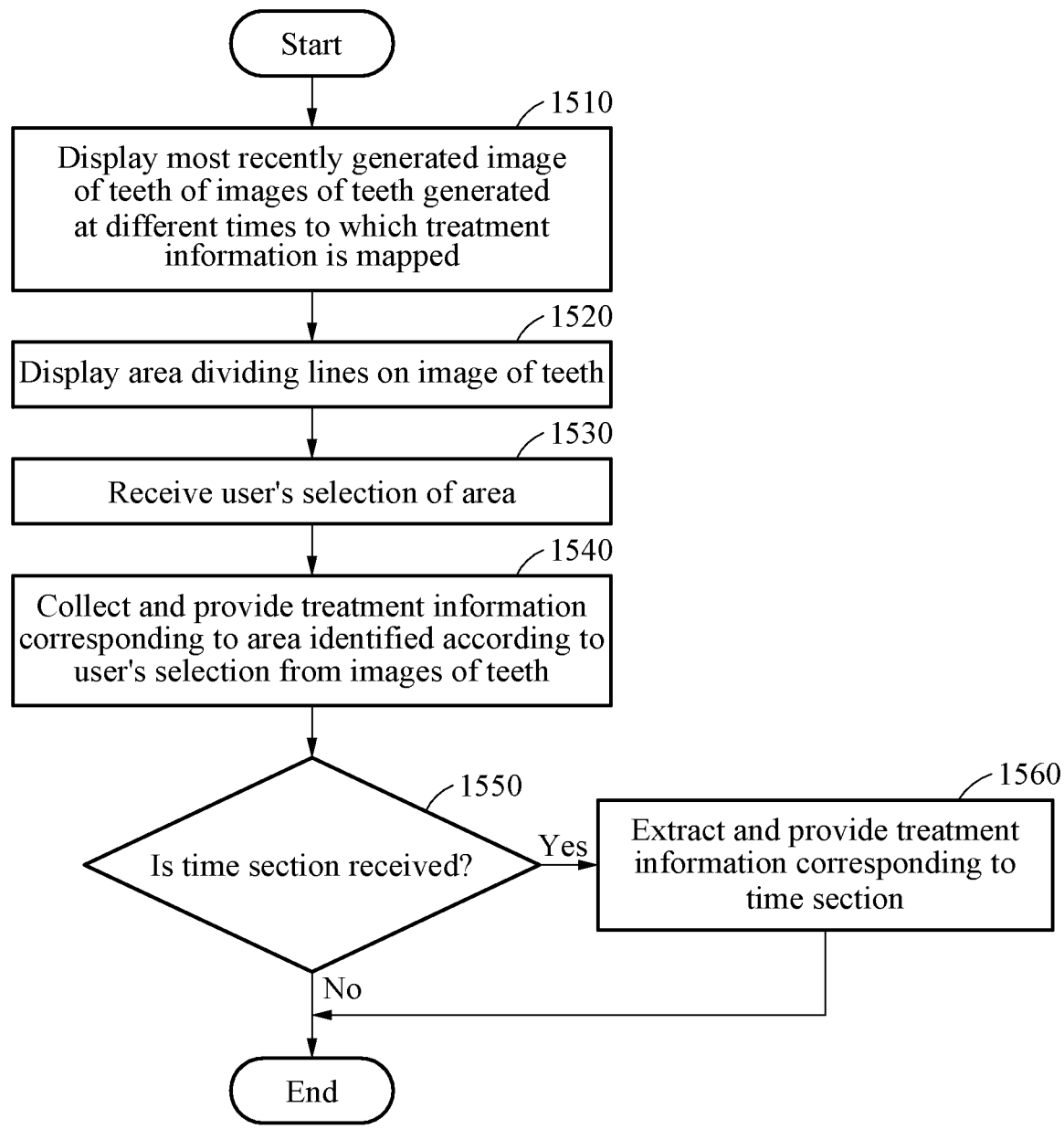
FIG. 15 is a flowchart illustrating a method for displaying pieces of treatment information displayed on a plurality of images of teeth in an accumulated manner according to an example embodiment.

FIG. 15 is a flowchart illustrating a method for displaying pieces of treatment information displayed on a plurality of images of teeth in an accumulated manner according to an example embodiment. Steps 1510 to 1560 of FIG. 15 may be included in step 1460 of FIG. 14 or may be performed independently of FIG. 14.

At step 1510, the treatment information display device 100 may identify the most recently generated image of teeth of the patient's images of teeth generated at different times and display the same on the display 101.

At step 1520, the treatment information display device 100 may display the area dividing lines on the image of teeth 102, each of the area dividing lines for dividing an area of each of teeth included in the image of teeth displayed at step 1510.

At step 1530, the treatment information display device 100 may receive the user's selection of any one of the plurality of areas divided according to the area dividing lines through the interface.

At step 1540, the treatment information display device 100 may collect treatment information of a tooth corresponding to the area corresponding to the user's selection from each of the patient's images of teeth generated at different times and provide the same to the user. In this case, the treatment information display device 100 may display pieces of the treatment information collected from each of the patient's images of teeth generated at different times on the most recently generated image of teeth in an accumulated manner.

At step 1550, the treatment information display device 100 may check whether time information including a time section is received from the user through the interface. In the case that the time information is received, the treatment information display device 100 may perform step 1560.

At step 1560, the treatment information display device 100 may extract pieces of treatment information corresponding to the time information from the pieces of treatment information displayed on the image of teeth at step 1540 and provide the same to the user. Specifically, the treatment information display device 100 may delete pieces of treatment information that does not correspond to the time information of the pieces of treatment information displayed on the image of teeth at step 1540 so that only pieces of treatment information corresponding to date information are displayed on the image of teeth.

According to example embodiments, it is possible to provide the user with a treatment history for each tooth by displaying the treatment information for the tooth in chronological order. Further, according to example embodiments, it is possible to enable the user to easily recognize which attribute of a treatment result of the past, a current status of the tooth, and a treatment plan for the tooth the treatment information corresponds to by varying the method of displaying the treatment information according to the attribute of the treatment information.

Further, according to example embodiments, it is possible to prevent an unnecessarily large amount of treatment information from obscuring the image of teeth by maintaining the number of pieces of treatment information displayed on the image of teeth below a predetermined number. In addition, according to example embodiments, the number of pieces of treatment information displayed in the same area may be increased by decreasing the size of each piece of treatment information displayed on the image of teeth.

The treatment information display method according to example embodiments may be embodied as a program that is executable by a computer and may be implemented as various recording media such as a magnetic storage medium, an optical reading medium, and a digital storage medium.

Various techniques described herein may be implemented as digital electronic circuitry, or as computer hardware, firmware, software, or combinations thereof. The techniques may be implemented as a computer program product, i.e., a computer program tangibly embodied in an information carrier, e.g., in a machine-readable storage device (for example, a computer-readable medium) or in a propagated signal for processing by, or to control an operation of a data processing apparatus, e.g., a programmable processor, a computer, or multiple computers. A computer program(s) may be written in any form of a programming language, including compiled or interpreted languages and may be deployed in any form including a stand-alone program or a module, a component, a subroutine, or other units suitable for use in a computing environment. A computer program may be deployed to be executed on one computer or on multiple computers at one site or distributed across multiple sites and interconnected by a communication network.

Processors suitable for execution of a computer program include, by way of example, both general and special purpose microprocessors, and any one or more processors of any kind of digital computer. Generally, a processor will receive instructions and data from a read-only memory or a random access memory or both. Elements of a computer may include at least one processor to execute instructions and one or more memory devices to store instructions and data. Generally, a computer will also include or be coupled to receive data from, transfer data to, or perform both on one or more mass storage devices to store data, e.g., magnetic, magneto-optical disks, or optical disks. Examples of information carriers suitable for embodying computer program instructions and data include semiconductor memory devices, for example, magnetic media such as a hard disk, a floppy disk, and a magnetic tape, optical media such as a compact disk read only memory (CD-ROM), a digital video disk (DVD), etc. and magneto-optical media such as a floptical disk, and a read only memory (ROM), a random access memory (RAM), a flash memory, an erasable programmable ROM (EPROM), and an electrically erasable programmable ROM (EEPROM). A processor and a memory may be supplemented by, or integrated into, a special purpose logic circuit.

Also, non-transitory computer-readable media may be any available media that may be accessed by a computer and may include both computer storage media and transmission media.

The present specification includes details of a number of specific implements, but it should be understood that the details do not limit any invention or what is claimable in the specification but rather describe features of the specific example embodiment. Features described in the specification in the context of individual example embodiments may be implemented as a combination in a single example embodiment. In contrast, various features described in the specification in the context of a single example embodiment may be implemented in multiple example embodiments individually or in an appropriate sub-combination. Furthermore, the features may operate in a specific combination and may be initially described as claimed in the combination, but one or more features may be excluded from the claimed combination in some cases, and the claimed combination may be changed into a sub-combination or a modification of a sub-combination.

Similarly, even though operations are described in a specific order on the drawings, it should not be understood as the operations needing to be performed in the specific order or in sequence to obtain desired results or as all the operations needing to be performed. In a specific case, multitasking and parallel processing may be advantageous. In addition, it should not be understood as requiring a separation of various apparatus components in the above described example embodiments in all example embodiments, and it should be understood that the above-described program components and apparatuses may be incorporated into a single software product or may be packaged in multiple software products.

It should be understood that the example embodiments disclosed herein are merely illustrative and are not intended to limit the scope of the invention. It will be apparent to one of ordinary skill in the art that various modifications of the example embodiments may be made without departing from the spirit and scope of the claims and their equivalents.

The invention claimed is:

1. A treatment information display method, the method comprising:
receiving a plurality of patient images of teeth for a plurality of patients at different times;
displaying at least one of the plurality of images from a first patient of the plurality of patients;
displaying area dividing lines on the displayed image of the teeth, each of the area dividing lines for dividing an area of each of the teeth included in the image of the teeth;
receiving, through an interface, a user selection of one of a plurality of areas divided according to the area dividing lines;
in response to the user selection, displaying an additional image of a tooth corresponding to the area;
identifying a received direction selected by a user on the additional image of the tooth through the interface; and
displaying at least one type of treatment information from different types of treatment information based on the identified direction selected by the user on the additional image of the tooth;
wherein the different types of treatment information of the tooth comprises treatment information of the tooth collected from each of the patient's images of the teeth generated at different times in an accumulated manner,
wherein the displaying the at least one type of treatment information of the tooth comprises:
displaying summary information if the number of pieces of the treatment information of the tooth in the accumulated manner is equal to or greater than a threshold value wherein the summary information is reduced in size compared to detailed information, and displaying detailed information in the accumulated manner if the number of pieces of the treatment information of the tooth is less than the threshold value.

2. The method of claim 1, further including mapping pieces of treatment information corresponding to time information received from the user of pieces of treatment information of the tooth corresponding to the area to an area corresponding to the user's selection and displaying the mapped pieces of treatment information corresponding to the time information received from the user to the area corresponding to the user's selection.

3. The method of claim 2, further including sorting the pieces of treatment information of the tooth corresponding to the area in chronological order, and selecting and displaying sequentially a preset number of pieces of information of the sorted pieces of treatment information.

4. The method of claim 1, wherein the at least one type of treatment information comprises the detailed information on treatment and the summary information in which the size of information displayed on a display is reduced compared to the detailed information by summarizing the detailed information.

5. The method of claim 1, wherein the at least one type of treatment information comprises at least one of past treatment information including a diagnosis history or a treatment history generated for the tooth at a previous time based on the time at which the image of the teeth is displayed, current treatment information including a diagnosis result for a current status of the tooth included in the image of the teeth, and future treatment information including a treatment plan to be performed for the tooth at a later time based on the time at which the image of the teeth is displayed.

6. The method of claim 1, further comprising:
receiving time information selected by the user through the interface; and
searching for a tooth for which the at least one type of treatment information is generated within a time section included in the time information, wherein the displaying of the area dividing lines on the displayed image of the teeth comprises displaying the area of the searched tooth to be differentiated from that of an unsearched tooth.

7. The method of claim 1, further comprising:
receiving time selected by the user through a navigation bar for allowing selection from the time at which the at least one type of treatment information is initially generated to the time at which treatment of the patient is expected to be completed,
wherein the providing the at least one type of treatment information of the tooth comprises selecting one of past treatment information, current treatment information, and future treatment information from the treatment information of the tooth corresponding to the area according to movement of the navigation bar and a position at which the navigation bar stops moving and displaying the selected one of the past treatment information, the current treatment information, and the future treatment information.

8. The method of claim 7, further comprising:
searching for a tooth for which the at least one type of treatment information is generated before a time corresponding to a position where the navigation bar stops moving,
wherein the displaying of the area dividing lines on the displayed image of the teeth comprises displaying the color of the area or the area dividing line of the searched tooth, and a display effect to be applied to the area of the tooth to be differentiated from those of the area of an unsearched tooth.

9. The method of claim 1, further comprising:
displaying a list of diagnosis types or treatment types;
receiving the users selection of a diagnosis type or a treatment type through the interface; and
searching for a tooth corresponding to the diagnosis type or treatment type selected by the user,
wherein the displaying of the area dividing lines on the displayed image of the teeth comprises displaying the color of the area or the area dividing line of the searched tooth, and a display effect to be applied to the area of the tooth to be differentiated from those of the area of an unsearched tooth.

10. The method of claim 1, further including displaying one of past treatment information, current treatment information, and future treatment information, and images related to the tooth corresponding to the area according to the direction selected by the user.

11. The method of claim 1, further including:
displaying summary information obtained by statisticizing past treatment information, current treatment information, and future treatment information of the tooth corresponding to the area;
in the case of receiving the user selection of the summary information through the interface, displaying one of a list of pieces of the past treatment information, a list of pieces of the current treatment information, and a list of pieces of the future treatment information according to the user selection; and
in the case that one of the pieces of treatment information included in the list is selected by the user, displaying detailed information about the piece of treatment information selected by the user.

12. A non-transitory computer-readable storage medium storing instructions that, when executed by a processor, cause the processor to perform the method of claim 1.

13. A treatment information display method, the method comprising:
displaying at least one of a plurality of images of a patient's teeth;
displaying area dividing lines on the image of the teeth, each of the area dividing lines for dividing an area of each of the teeth included in the image of the teeth;
receiving, through an interface, a user selection of any one of a plurality of areas divided according to the area dividing lines from a patient's image of the teeth;
overlapping and displaying on the image of the teeth an animation image of the tooth corresponding to the selected area;
identifying a position, angle, or shape of the tooth in which the tooth is to be corrected according to a treatment plan corresponding to at least one type of different types of treatment information mapped to the selected tooth; and
wherein the animation image animates a process of changing the tooth from a current state to the position, angle, or shape of the tooth of a corrected state according to the at least one type of mapped treatment information.

14. The method of claim 13, wherein the at least one type of treatment information comprises detailed information on treatment and summary information in which the size of information displayed on a display is reduced compared to the detailed information by summarizing the detailed information, and
the at least one type of treatment information comprises, if the number of pieces of the at least one type of treatment information of the tooth corresponding to the area is equal to or greater than a threshold value, providing the user with the summary information, and if the number of pieces of the at least one type of treatment information of the tooth corresponding to the area is less than the threshold value, providing the user with the detailed information.

15. A treatment information display device, the device comprising:
a display configured to display a plurality of images of teeth for a plurality of patients at different times and display area dividing lines on the displayed image of the teeth, each of the area dividing lines for dividing an area of each of the teeth included in the image of the teeth; and
a processor configured to receive a user selection of one of a plurality of areas divided according to the area dividing lines through an interface, to display, in response to the user selection, an additional image of a tooth corresponding to the area, receive a direction selected by a user on the additional image of the tooth through the interface, and to display at least one type of treatment information from different types of treatment information based on the direction selected by the user,
wherein the different types of treatment information of the tooth comprises treatment information of the tooth collected from each of the patient's images of the teeth generated at different times in an accumulated manner, and
wherein the processor configured to:
display summary information if the number of pieces of the at least one type of treatment information of the tooth in the accumulated manner is equal to or greater than a threshold value wherein the summary information is reduced in size compared to detailed information, and display detailed information if the number of pieces of the at least one type of treatment information of the tooth in the accumulated manner is less than the threshold value.

16. A treatment information display device, the device comprising:
a processor configured to:
display at least one of a plurality of images of a patient's teeth;
display area dividing lines on the image of the teeth, each of the area dividing lines for dividing an area of each of the teeth included in the image of the teeth;
receive through an interface a user selection of any one of the plurality of areas divided according to the area dividing lines from a patient's image of the teeth; and
overlap and display on the image of the teeth an animation image of the tooth corresponding to the selected area,
wherein the processor is configured to identify a position, angle, or shape of the tooth in which the tooth is to be corrected according to a treatment plan corresponding to at least one type of different types of treatment information mapped to the selected tooth; and
wherein the animation image animates a process of changing the tooth from a current state to the position, angle, or shape of the tooth of a corrected state according to the at least one type of treatment information.

* * * * *